(12) United States Patent
Hatfield et al.

(10) Patent No.: US 7,319,942 B2
(45) Date of Patent: Jan. 15, 2008

(54) MOLECULAR CONTAMINANT FILM MODELING TOOL

(75) Inventors: David Brooke Hatfield, Oracle, AZ (US); Michael Kennedy Burkland, Tucson, AZ (US); Elaine Ellen Seasly, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 701 days.

(21) Appl. No.: 10/723,337

(22) Filed: Nov. 26, 2003

(65) Prior Publication Data

US 2005/0114101 A1    May 26, 2005

(51) Int. Cl.
*G06F 7/60* (2006.01)
(52) U.S. Cl. ............................. 703/2; 438/14; 438/16; 703/6
(58) Field of Classification Search ................. 703/13, 703/2, 6; 438/14, 16
See application file for complete search history.

(56) References Cited

U.S. PATENT DOCUMENTS

| | | |
|---|---|---|
| 3,654,109 A | 4/1972 | Hohl et al. |
| 5,710,418 A | 1/1998 | Tawara |
| 6,046,451 A | 4/2000 | Sinha et al. |
| 7,053,355 B2 * | 5/2006 | Ye et al. .................. 250/208.1 |
| 2003/0063284 A1 | 4/2003 | McAndrew et al. |
| 2003/0068834 A1 * | 4/2003 | Kishkovich et al. .......... 438/14 |

FOREIGN PATENT DOCUMENTS

| | | |
|---|---|---|
| EP | 0 710 830 A | 5/1996 |
| JP | 2001-110698 A | 4/2001 |
| JP | 2002-168776 | 6/2002 |

OTHER PUBLICATIONS

International Search Report regarding Application No. PCT/US2004/035787 mailed Feb. 24, 2005.

* cited by examiner

*Primary Examiner*—Paul Rodriguez
*Assistant Examiner*—Nithya Janakiraman
(74) *Attorney, Agent, or Firm*—Renner, Otto, Boisselle and Sklar, LLP

(57) ABSTRACT

A system and method for modeling the effect of a molecular contaminant film on performance of an optical system is disclosed. A mass of material outgassed from materials of the optical system is correlated to spectrum of outgassed products. The spectrum of outgassed products is normalized, and an aggregate molecular contaminant film thickness is predicted from each material. The absorbance spectrum of the aggregate molecular contaminant film is derived, and the derived absorbance spectrum of the aggregate contaminant film is convolved with an optical system instrument function. A plot of at least one transmission band as a function of source temperature is performed to determine the degradation in performance of the optical system.

35 Claims, 17 Drawing Sheets

Synthetic spectrum - Uralane

| Vector | thickness (microns) | Class of contaminant |
|---|---|---|
| N,N-diethylanliline | 0.30 | Aromatic amine |
| polyethyleneglycol | 0.40 | polyether |
| 1-pentanol | 0.30 | Aliphatic alcohol |
| dioctylphthalate | 0.05 | Aromatic ester |
| dioctyl sebecate | 0.05 | Aliphatic ester |
| Octanoic acid | 0.05 | Aliphatic carboxylic acid |
| n-nonane | 0.00 | Aliphatic hydrocarbon |
| Total thickness | 1.15 | |

| Vector | Applied thickness | Density | Density weighted thickness A |
|---|---|---|---|
| | (microns) | (g cm$^{-3}$) | (micron g cm$^{-3}$) |
| N,N-diethylanliline | .30 | 0.94 | 0.282 |
| Polyethylene glycol | .40 | 1.1 | 0.440 |
| 1-pentanol | .35 | 0.81 | 0.284 |
| dioctyl phthalate | .05 | 0.97 | 0.048 |
| dioctyl sebecate | .05 | 0.91 | 0.046 |
| Octanoic acid | .05 | 0.91 | 0.046 |
| n-nonane | -0.50 | 0.72 | -0.360 |
| sum | 0.70 | 6.36 | 0.79 |
| Equivalent thickness | 0.70 (micron) | N/A | 0.87 (micron) |

| Soil | Volume Of material (cm³) | Density Of material (g cm⁻³) | CVCM Of material (% m/m) | Density of CVCM (g cm⁻³) | Estimated volume of CVCM / NVR (cm³) | Estimated thickness Of CVCM/ NVR (nm) |
|---|---|---|---|---|---|---|
| outgassing Adhesive 1 | 2.5 | 1.0 | 0.05 | 1.0 | $1.2 \times 10^{-3}$ | 1.5 |
| Polymer A | 60 | 1.5 | 0.005 | 1.0 | $4.5 \times 10^{-3}$ | 5.6 |
| NVR Hydrocarbon | 0.080 | 1.0 | 1.00 | 1.0 | $8.0 \times 10^{-2}$ | 100 |

370 → Volume Of material; 372 → Density Of material; 374 → CVCM Of material; 376 → Density of CVCM; 378 → Estimated volume of CVCM / NVR; 380 → Estimated thickness Of CVCM/ NVR

FIG. 15

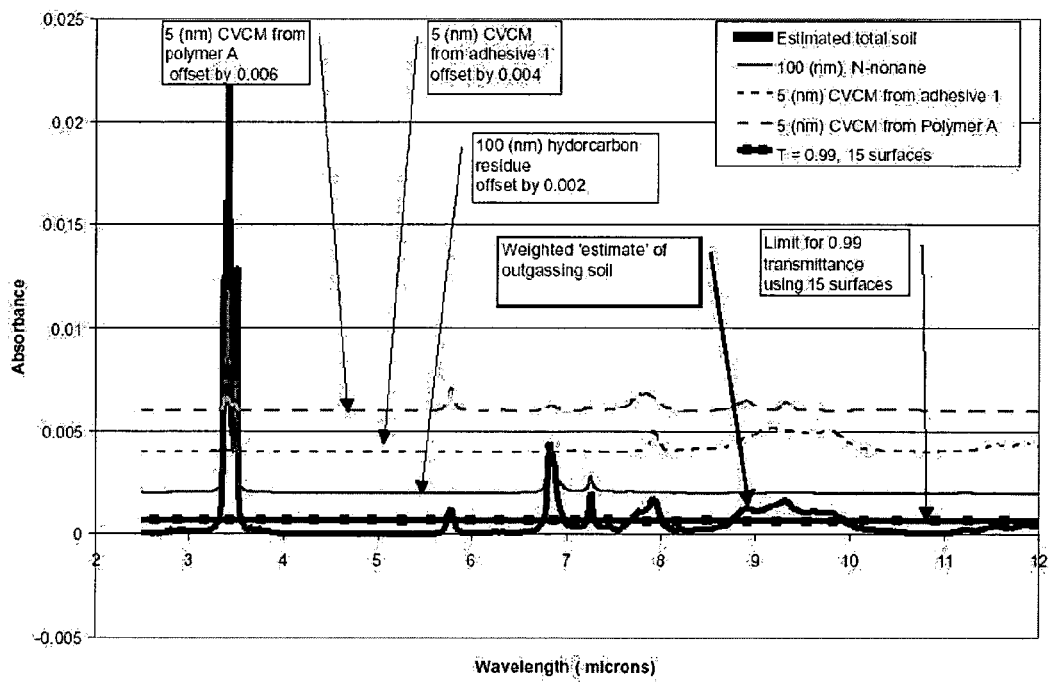

FIG. 16

Band 1 Transmittance

MOLECULAR CONTAMINANT FILM MODELING TOOL

FIELD OF THE INVENTION

The present invention relates to molecular contaminant films, and more particularly, to a system and method for modeling the effect of molecular contaminant films on optical systems caused by outgassing of materials.

BACKGROUND OF THE INVENTION

Optical systems are systems that employ optical lenses, mirrors, sensors, e.g., infrared sensors and the like, etc., to monitor a specified parameter. To optimize the performance of optical systems, it is desirable that the optics within the system be free from contaminants that can interfere with the lens's, sensor's, etc., performance. Contaminants, as used herein, include airborne molecular contamination (AMC), which also is referred to as a Collectable Volatile Condensable Material (CVCM), e.g., a soil. As is known in the art, AMCs cover a wide range of contaminants present in the air and can lead to contamination in the form of chemical films, sometimes as thin as a single molecule.

AMCs can cause yield losses due to changes in the chemical, electrical, optical, and physical properties of product surfaces. As contaminants accumulate on optical surfaces, the contaminants physically absorb and scatter incoming light, thus distorting the quality of the spherical wavefront. When the information contained in the spherical wavefront is distorted, the resulting image also is malformed and the overall performance of the optical system is degraded.

Every material introduced into a system is a potential source of AMCs. The chemical composition of a material, its surface area and its use temperature ultimately determine the levels of contamination introduced into the system. The contaminants can be introduced through numerous means, the most common of which being through contaminants on subcomponents, contaminants introduced during assembly of the optical system, e.g., assembly of the subcomponents, and contaminants introduced from outgassing of materials within the subcomponents.

As is known in the art, outgassing is the evolution of embedded substance, with a non-zero vapor pressure from a material over time. Outgassing occurs when a material is placed in a low pressure environment and can be accelerated under conditions of elevated temperature. As a material undergoes outgassing, some of its constituents are volatilized and the material experiences a weight loss, measured as percent total weight loss, and a certain percentage of the volatile constituents are condensable upon nearby surfaces. This second property is the more critical, as the condensable matter may contaminate sensitive optical or thermal control surfaces.

In designing and manufacturing optical systems, it is desirable to know the end life (e.g., worst case) contamination that can be introduced into the system. With such information in hand, the effects of design and manufacturing changes on the performance of a device can readily be ascertained without the need to physically construct and test the device.

Estimating the effect of outgassing products on the end of life performance of optical systems requires knowledge of the absorption coefficient of the aggregate outgassing soil as a function of wavelength associated with an aggregate film thickness. An aggregate film, as used herein, is a contaminant film that is formed from the combination of all soils outgassed within a system. One approach to solving this problem is to estimate the contribution of each individual material present to the aggregate soil. This approach requires that a spectrum, such as an infrared spectrum, be acquired from a sample of outgassing soil from each individual material, where the thickness of the corresponding soil sample is known. Unfortunately, the thickness of the soil sample usually is not known, and thus estimating the contribution of each individual material present to the aggregate soil is not feasible.

Conventional methods have attempted to estimate the thickness of each individual film. Unfortunately these methods have proven to be ineffective for molecular contaminant films that exceed 10 nanometers in thickness. Additionally, conventional methods do not consider the chemical composition of the total aggregate molecular contaminant film. As a result, such methods are of limited use, since accuracy falls off sharply as variations in chemical composition of the contaminant film increase.

Accordingly, there is a need the art for a system and method that accurately models the spectral character of a molecular contaminant film based on the components that generate the film. Additionally, it would be advantageous for such a system and method to consider the chemical composition of the aggregate of the molecular contaminant film in modeling the molecular contaminant film.

SUMMARY OF THE INVENTION

In the light of the foregoing, one aspect of the invention relates to a method of modeling the effect of a molecular contaminant film on performance of an optical system, including the steps of: correlating a mass of material outgassed from materials of the optical system to spectrum of outgassed products; normalizing the infrared spectrum of outgassed products; predicting an aggregate molecular contaminant film thickness from each material; deriving an absorbance spectrum of the aggregate molecular contaminant film; and convolving the absorbance spectrum of the aggregate molecular contaminant film with an instrument function of the optical system.

Another aspect of the invention relates a method of obtaining a per unit absorbance spectrum of a contaminant film when the thickness of the film is unknown, including the steps of: collecting outgassed material from a compound; classifying the outgassed material into one of several groups based on at least one observed characteristic of the outgassed material; obtaining an absorbance spectrum of a sample of the outgassed material; estimating a thickness of the sample of outgassed material based on the absorbance spectrum and the classification of the outgassed material; and scaling the absorbance spectrum of the sample of outgassed material by the estimated thickness of the sample of outgassed material.

Yet another aspect of the invention relates a computer system for modeling the effect of a molecular contaminant film on performance of an optical system, including: a storage medium; at least one processor, wherein the processor is operatively coupled to the storage medium; a computer program residing on the storage medium and executed by the at least one processor, wherein the computer program causes the processor to correlate a mass of material outgassed from materials of the optical system to spectrum of outgassed products; normalize the infrared spectrum of outgassed products; predict an aggregate molecular contaminant film thickness from each material; and convolve an absorbance spectrum of the aggregate molecular contaminant film with an optical system instrument function.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 15 illustrates exemplary computations for estimating film thickness from outgassing data in accordance with an embodiment of the present invention;

FIG. 16 illustrates the spectral characteristics for each soil listed in FIG. 15 weighted by the final thickness expected for each soil in accordance with an embodiment of the present invention;

DESCRIPTION OF THE INVENTION

Figure 1A:
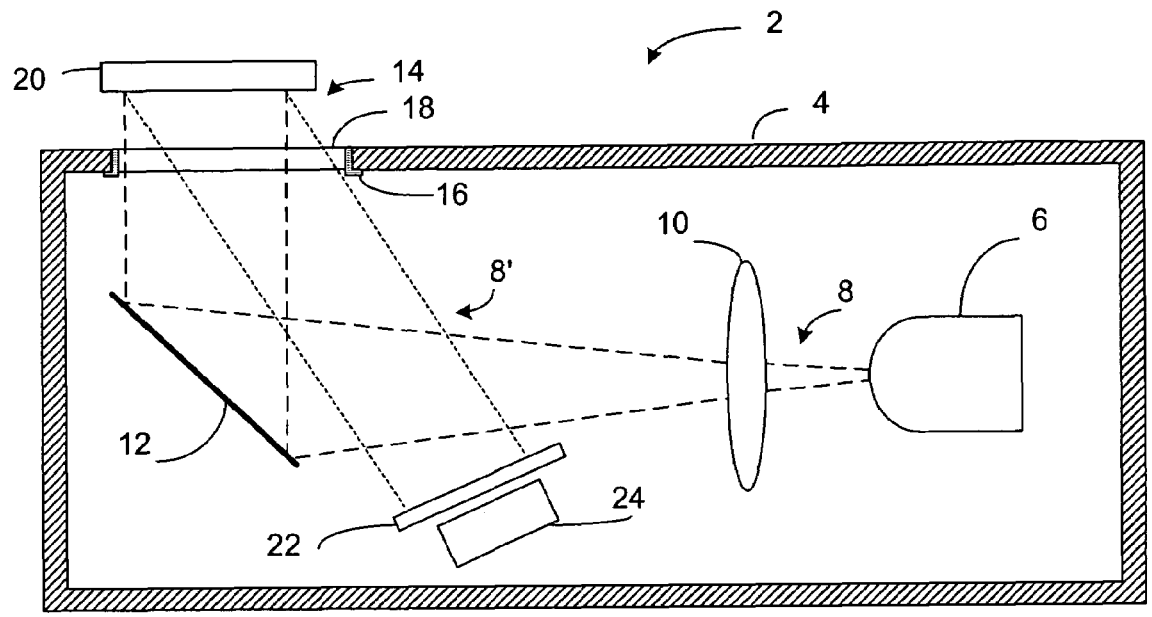
FIG. 1A is an isometric diagram of an exemplary optical sensor.

The following is a detailed description of the present invention with reference to the attached drawings, wherein like reference numerals will refer to like elements throughout.

The invention is discussed with respect to a sensor, such as an optical sensor, for example. It should be appreciated, however, that the invention can be applied to other optical systems and/or optical components that may be detrimentally affected by contaminant films, and its discussion with respect to a sensor is not intended to be limiting in any way.

Referring to FIG. 1A, an isometric view of an exemplary optical sensor 2 is shown. The optical sensor includes a housing 4, which can be a rigid plastic material, for example. Mounted within the housing is a high intensity broad spectrum light source 6, which produces a beam 8 of light that is highly collimated. A lens 10 focuses the beam 8 on a mirror 12, which reflects the beam 8 through an aperture 14. The aperture 14 is sealed by an O-ring 16 and a transparent shield 18, such as a clear plastic lens, for example. The beam 8 strikes an object of interest 20, and a portion of the beam 8' is reflected back towards the sensor 2 and through the aperture 14. The returning beam 8' follows a direct path from the aperture 14 to a focusing means 22 for focusing the beam 8' on a light sensitive surface of a light detector 24.

Figure 1B:
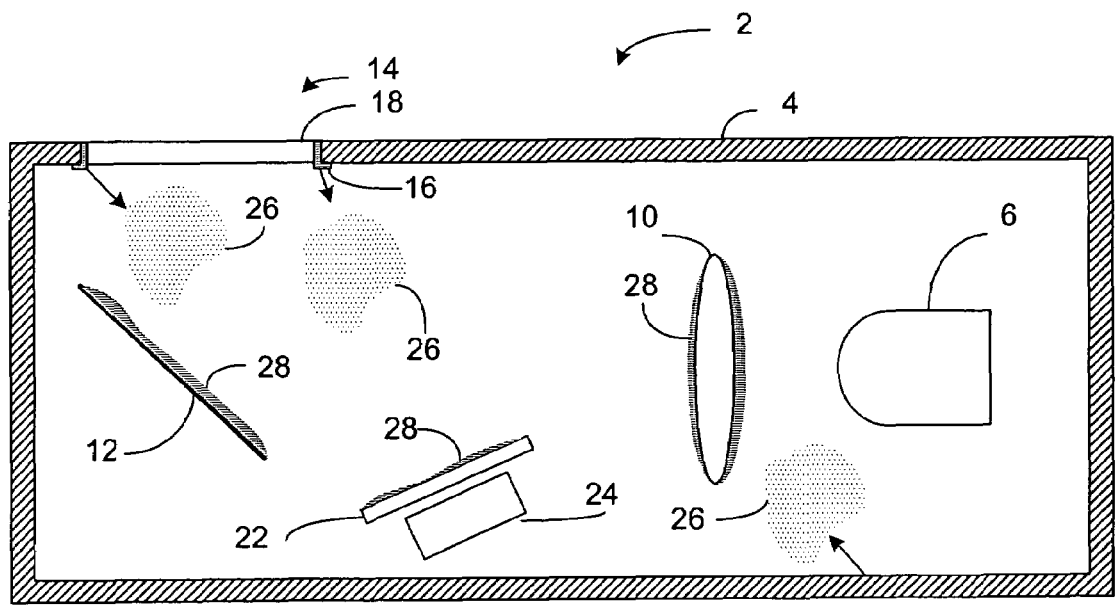
FIG. 1B is an isometric diagram of an exemplary optical sensor illustrating outgassing of materials and accumulation of a film on optical components.

Over time, soils outgas from materials within the sensor, such as organic materials, and can settle on nearby components. Generally, the outgassed soils are of little concern for most applications. In optical systems, however, the soils can interfere with the performance of the optical system. Referring to FIG. 1B, soils 26 are shown outgassing from the rubber O-ring 16 and from the housing 4. The soils accumulate on nearby surfaces, such as the lens 10, mirror 12 and focusing means 22, to form a contaminant film 28 on each respective surface. The contaminant film 28 can interfere with the transmission of the beam 8, 8' (see FIG. 1A) of light, thus degrading performance of the optical sensor. If the degradation becomes excessive, the sensor 2 can fail to operate within a desired performance window, resulting in erroneous operation and/or data. In some instances, the degradation in performance may be so severe that the sensor 2 fails to operate altogether.

The present invention relates to a system and method of estimating the degradation in performance of an optical system. As will be described in more detail below, the system of the present invention constructs an absorbance spectrum of the aggregate contaminant film, and the effect the aggregate contaminant film has on sensor or other optical performance is estimated.

Figure 2A:
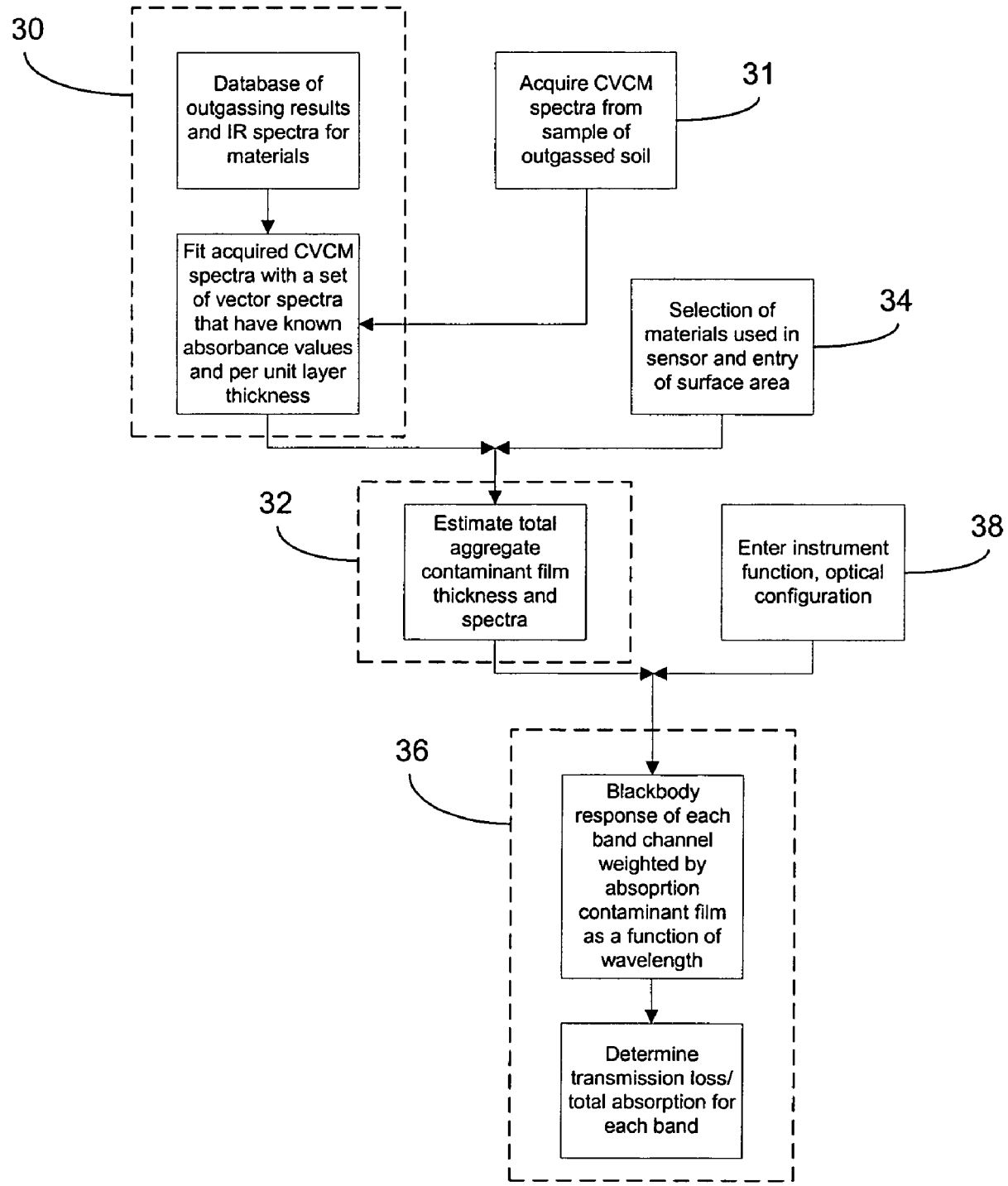
FIG. 2A is a block diagram providing an overview of system functionality and user input in accordance with an embodiment of the present invention.

Referring to FIG. 2A, an overview of an exemplary system for estimating the degradation in optical system performance due to outgassing is shown. The system includes 3 modules, each of which performs one or more tasks that are used to estimate the degradation in optical system performance. A first module 30 includes a database of outgassing results and IR spectra for known material having a unit layer thickness. The database of outgassing results and IR spectra are entered into the system based on outgassing tests performed on known compounds and materials. As shown at block 31, the designer of the sensor acquires Collected Volatile Condensable Material (CVCM) spectra for compounds used in constructing the sensor. The acquired CVCM spectra are entered into the first module 30. As will be described in more detail below, the CVCM spectra are acquired using a modified form of the ASTM E595 test, and the results of the tests are stored in the database of the first module 30. Using the database of outgassing results, the acquired CVCM spectra, and a method of estimating an equivalent thickness of a soil sample used to obtain the CVCM spectra in accordance with the present invention, the first module 30 estimates an absorbance spectrum per unit thickness (i.e., a normalized spectrum) for each compound used to construct the sensor. The estimated per unit absorbance spectrum is stored in the database of the first module.

A second module 32 estimates an aggregate contaminant film thickness that can be produced from all outgassed soils within the optical system. Additionally, the second module derives an absorbance spectrum of the aggregate contaminant film. The second module estimates the aggregate film thickness and absorbance spectrum using the per unit absorbance spectra stored in the first module 30, along with specific information relating to the optical system, e.g., the compounds used to construct the optical system, their mass, volume, etc. The specific information relating to the optical system is entered into the second module by the designer of the optical system, for example, as shown in block 34. Based on the entered information and the data stored in the first module, the system constructs an absorbance spectrum of the aggregate contaminant film and estimates the aggregate contaminant film thickness.

A third module 36 estimates the degradation in performance of the optical system due to the aggregate contaminant film. An optical configuration of the optical system and an instrument function of the optical system are entered by the designer into the third module, as shown in block 38. Using the entered optical system data along with the data generated by the second module, the third module estimates the transmission loss and total absorption that could occur in the optical system.

Figure 2B:
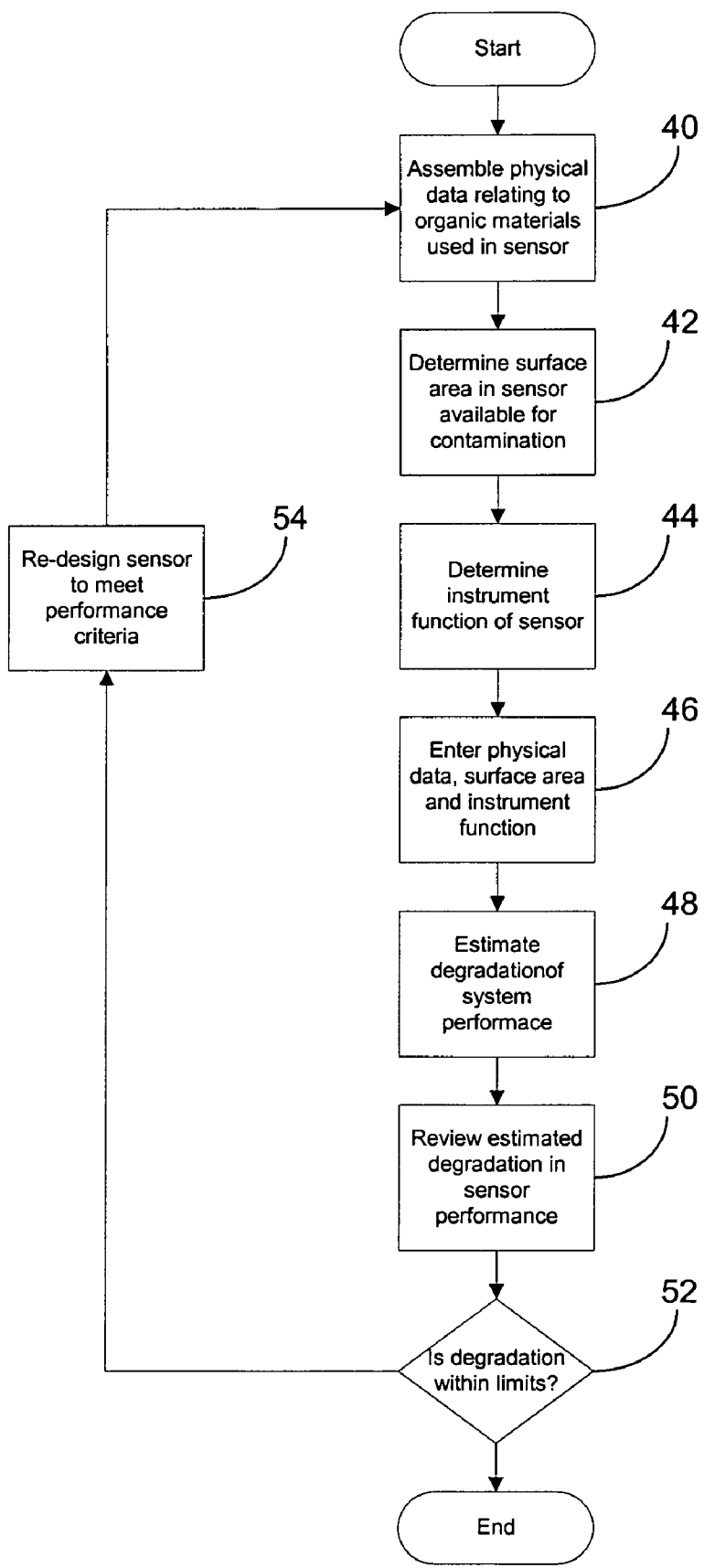
FIG. 2B is a flow diagram illustrating an exemplary use of the present invention.

Referring to FIG. 2B, a flow chart illustrating one use of the present invention is shown. Beginning at step 40, the designer assembles physical data relating to materials used in constructing the sensor. The physical data includes, for example, the materials that make up the sensor, the mass of each material and its respective volume. In the exemplary sensor of FIG. 1A, the physical data would include the mass and volume of the O-ring 16, the transparent shield 18, and the housing 4, and the materials that make up the respective components, for example. Outgassing tests are performed on the materials, preferably using a modified for of the ASTM E595 test (discussed below). After assembling the data relating to the materials, the designer determines the surface area within the sensor that is available for contamination, as shown at step 42. The surface area can be determined, for example, by simple geometry. At step 44 the designer determines the instrument function of the sensor 2. The instrument function is the instrument's (e.g., sensor's) efficiency in turning a known amount of light into a known signal. It can be determined, for example, by measuring the intensity of the source signal, and measuring the intensity loss through the sensor.

The designer enters the accumulated data (physical data, outgassing data, surface area and instrument function), into a system in accordance with the invention at step 46, and the system estimates the worst case performance degradation the sensor can encounter due to outgassing at step 48. At step 50, the estimated degradation in performance is presented to the designer and at step 52 the designer may make a decision as to whether the performance degradation is acceptable. If it is acceptable, then the process is complete. If it is not acceptable, then at step 54 the designer may alter or redesign portions of the sensor. For example, a different type of plastic may be used for the housing 4 or an O-ring 16 having a different rubber composition may be employed. After the design change, the process returns to step 40 and is repeated until acceptable results are obtained.

The present invention estimates the optical degradation of a sensor by convolving the absorbance spectrum of the aggregate contaminant film with the instrument function of the sensor. In determining the absorbance spectrum of the aggregate contaminant film, the invention obtains an average absorbance spectrum from a sample of each outgassed soil, and estimates an equivalent thickness of the respective soil sample used to obtain the absorbance spectrum. According to the present invention, the method of estimating the equivalent thickness for a particular soil sample is dependant on the type of soil. Contaminant soils are classified into one of three groups: 1) contaminants that are a pure substance and are in liquid form at room temperature; 2) contaminants that are not a liquid or a pure substance, but an infrared spectrum indicates that the absorbance in the region(s) of interest is dominated by a single functional group; and 3) contaminants in which the outgassing products are not a pure substance and cannot be represented by a single model compound that is a liquid. Depending on the type of soil, one of the three methods is implemented to estimate the equivalent thickness of the soil sample. The average absorbance spectrum of the soil is divided by the estimated thickness of the soil sample to obtain an absorbance spectrum per unit thickness of the soil sample.

The per unit absorbance spectrum is used to construct a spectrum of the aggregate film that can accumulate due to outgassing of various materials used within the sensor. The effect of the aggregate contaminant film on sensor performance is estimated by convolving the absorbance spectrum of the aggregate film with the instrument function of the sensor. The result is an estimate of the worst case transmission loss that the sensor could experience due to the presence of molecular film contamination from outgassing.

Each of the three types of soils and the respective method of estimating the equivalent soil thickness now will be discussed.

Type 1—Contaminants that are a Pure Substance and are in Liquid Form at Room Temperature The first type of soil is a contaminant that is a pure substance in liquid form at room temperature, such as Dioctyl Phthalate. When working with a Type 1 soil, basic information about the soil sample, such as the mass of the soil sample and the area the soil sample occupies, is assembled.

The mass of the soil sample can be determined by weighing the soil sample. For example, two infrared (IR)

salt plates are weighed, preferably to the nearest 0.01 milligram, and a small quantity of the soil sample is placed on one plate. The soil sample then is squeezed between both plates to form a spot about two centimeters in diameter. The plates are reweighed and the mass of the soil sample is calculated as the difference between the mass of the sample and the salt plates minus the mass of the salt plates alone.

After the mass of the soil sample is determined, a set of infrared transmission spectra are acquired using a Fourier-transform infrared spectrophotometer, for example. Preferably, five infrared transmission spectra are acquired, and each sample is rotated between each measurement. An average absorbance spectrum is prepared from the set of observations to obtain an optical average of the soil sample as is conventional. The spectrum is baseline corrected in transmission mode, with the final result converted to absorbance (log 10), and any atmospheric doublet that may be present is removed. Preferably, the transmission should not be less than about 20% for any measurement. If the transmitted intensity is below 20%, another sample should be prepared.

$$\text{Thickness} = \frac{\text{Mass}}{\text{Density} \times \text{Area}} \qquad \text{Equation 1}$$

The thickness of the soil sample can be computed using Equation 1. Thickness is defined as the thickness of the sample in centimeters, Mass is defined as the mass of the sample in grams, Density is defined as the density of the sample in grams per cubic centimeter, and Area is defined as the area occupied by the sample in square centimeters. As described above, the mass of the soil sample is determined from measurements, and the density of the soil sample is known either by measurement or by established densities for pure materials. The area occupied by the soil sample is obtained using basic geometry, as is described below with respect to Equation 2 and Equation 3.

$$\text{Area} = \frac{\pi \times D^2}{4} \qquad \text{Equation 2}$$

$$\text{Area} = \frac{\pi \times D_{Major} \times D_{Minor}}{4} \qquad \text{Equation 3}$$

The area occupied by the soil sample is computed assuming the sample to be a perfect circle and applying Equation 2, where D is defined as the measured diameter of the soil sample in centimeters and Area is defined as the surface area occupied by the soil sample in square centimeters. If the sample is not circular, e.g., it is elliptical, then the area of the soil sample can be computed using the length of the major axis of the ellipse and the length of the minor axis of the ellipse. Equation 3 describes the calculation of the area of an ellipse, where $D_{Major}$ is defined as the length of the ellipse's major axis in centimeters, $D_{Minor}$ is defined as the length of the ellipse's minor axis in centimeters, and Area is defined as the surface area in square centimeters. The diameter and/or major/minor axis can be measured, preferably to the nearest millimeter, using a steal rule, for example. Once the Area, Density and Mass of the soil sample are obtained, the thickness of the soil sample can be calculated using Equation 1. A per unit absorbance spectrum of the soil sample is derived by dividing the average absorbance spectrum of the soil sample by the calculated thickness of the soil sample.

It is noted that the application of Equations 1-3 makes several assumptions. These assumptions briefly are discussed below along with any issues that may arise if the assumptions are violated.

First, the soil sample is assumed to have a low volatility. If the soil sample does not have a low volatility, then the film will evaporate quickly, which can cause inaccurate thickness calculations. Additionally, it is assumed the density of the soil sample is known or can be determined. If the density is not known or cannot be determined, then the thickness of the film cannot be computed.

It also is assumed that the soil sample has a moderate viscosity. If the soil sample has a high viscosity, then the sample will be too thick and a sample of uniform thickness will be difficult to obtain. If the viscosity is too low, then the soil sample may flow off the salt plate, thus invalidating the mass measurement of the soil sample.

Finally, it is assumed that the absorbance of the soil sample is linear with respect to thickness. Thick soil samples can cause rounding of peaks and low attenuation due to self absorbance. Peak transmittance greater than twenty percent generally is sufficient to control self absorbance.

Accordingly, through the use of simple geometry and spectroscopy, the thickness of a Type 1 soil sample and its transmission spectra are acquired. The absorbance spectrum per unit thickness is derived by dividing the average absorbance spectrum of the soil sample by the calculated soil sample thickness.

Type 2—Contaminants that are not a Liquid or a Pure Substance, but an Infrared Spectrum Indicates that the Absorbance in the Region(s) of Interest is Dominated by a Single Functional Group The second type of soil is a contaminant that is not a liquid or a pure substance, but an infrared spectrum of the soil indicates that the absorbance in the region(s) of interest is dominated by a single functional group. Outgassing products from Butyl rubber (e.g., butyl O-rings) are an example of this type of soil.

Outgassing products obtained from some butyl O-rings generally are solid and form crystals. It is very difficult to prepare a measurable, uniform layer of such a solid material and obtain a spectrum that has an absorbance that is scalable. The functional groups commonly observed by infrared absorption spectrophotometery in Type 2 soils have very large transitional probabilities. Care must be taken to ensure that the linearity assumption remains valid. Linearity is based on the Beer-Lambert relation (discussed below).

As will be described in more detail below, the absorbance spectrum per unit thickness of a Type 2 soil is estimated by selecting a material that has an absorbance spectrum with similar characteristics as a measured absorbance spectrum of a soil sample. Using a scale factor, the absorbance spectrum of the similar material is scaled to fit the measured absorbance spectrum of the soil sample, and an absorbance spectrum per unit thickness of the soil sample is estimated by dividing the measured absorbance spectrum by the scale factor. The process of scaling the measured absorbance spectrum by the scale factor does not violate the Beer-Lambert relation, as is discussed below with respect to Equation 4 and Equation 5.

$$\text{Abs} = a \times b \times c \qquad \text{Equation 4}$$

The absorbance of a film can be calculated using Equation 4, wherein a is defined as the absorption coefficient in liter per mole*centimeter, b is defined as the path length (i.e., film thickness) in centimeters, c is defined as the concentration in moles per liter, Abs is the absorbance, which is defined as $-\log_{10}(I/I_0)$, I is defined as the incident intensity in watts per square centimeter, and $I_0$ is defined as the transmitted intensity in watts per square centimeter.

$$\frac{Abs}{b} = a \times c \quad \text{Equation 5}$$

Dividing both sides of Equation 4 by the path length b results in Equation 5. Thus, according to the Beer-Lambert relation, the product a×c is the absorbance per unit thickness. Accordingly, the absorbance spectrum per unit thickness can be calculated by dividing the measured absorbance spectrum by the film thickness, as shown in Equation 5, without violating the Beer-Lambert relation.

Four basic assumptions are made in support of the Beer-Lambert relation. First, the soil sample is assumed to be dilute with no interaction between absorbers. Second, all absorbers are assumed to be in the ground state (excessive absorption can lead to a ground state population smaller than the concentration (Boltzman distribution)). Third, any light re-emitted after absorption is assumed not to be reabsorbed, or in other words, each photon can interact with the system only once. Finally, it is assumed that light is not scattered out of the system and light is not scattered or re-emitted into the beam path. Any light loss is due to absorption.

Typically, it is assumed that a pure substance has a constant concentration so that the product a×c is an effective absorption coefficient $\alpha(\lambda)(\text{cm}^{-1})$. Care must be taken when using literature values of absorption coefficients because published values may be computed using $\log_{10}$ or $\log_e$ (In) of the intensity ratio.

As stated above, the thickness of the soil sample is determined by using a known material that has similar characteristics as the soil sample. Thus, the characteristics of the soil sample must be determined before a selection of a similar material can be made.

The characteristics of the soil sample can be determined by obtaining an infrared absorbance spectrum of the soil sample. Once the absorbance spectrum is obtained, strong absorption features in the spectrum are identified, e.g., peaks in the absorbance spectrum.

Based on knowledge of infrared spectroscopy and chemistry, a selection is made of a material that has similar absorption features as the soil sample, and an infrared absorbance spectrum of a 1.0 micron thick layer of the selected material is obtained. The absorbance spectrum of the 1.0 micron thick layer of selected material then is overlaid with the absorbance spectrum of the soil sample and, if necessary, the selected material absorbance spectrum is scaled to conform to the shape of the soil sample absorbance spectrum.

The absorbance spectrum of the soil sample then is scaled by dividing the soil sample spectrum by the scale factor applied to the absorbance spectrum of the selected material. The scaling of the soil sample spectrum produces an estimate of an absorbance spectrum for a 1.0 micron thick layer of the soil sample.

Figure 3:
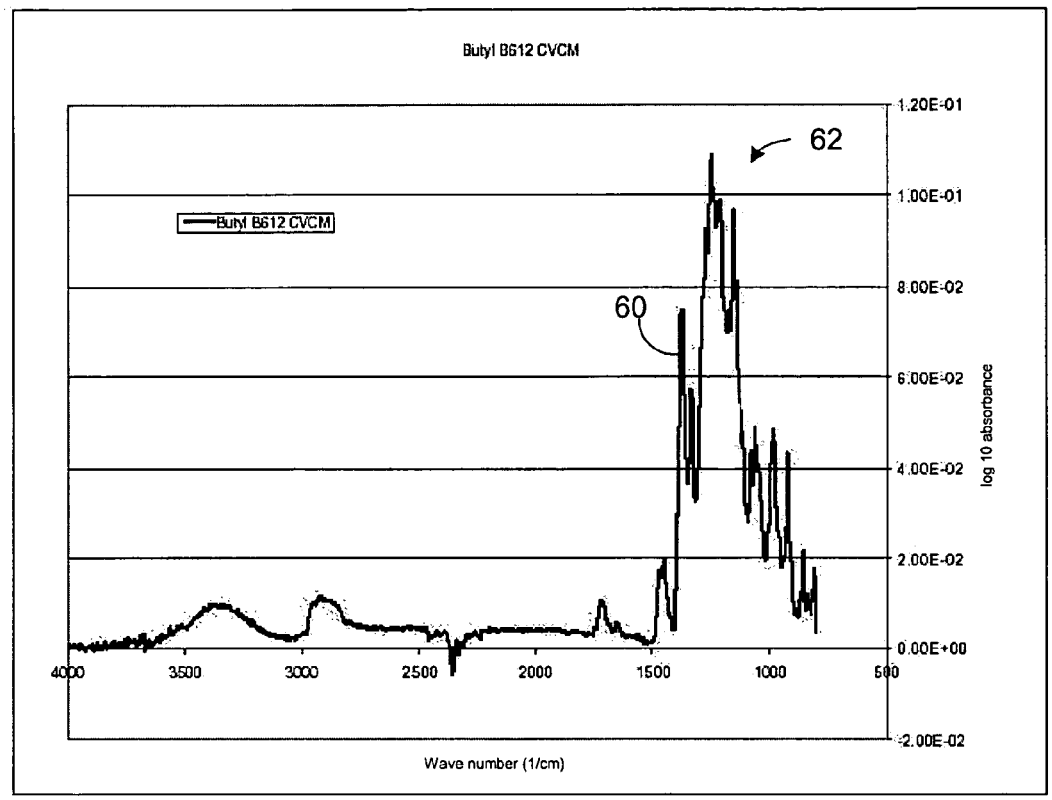
FIG. 3 is an infrared spectrum acquired from a sub-sample of outgassed products of Butyl Rubber.

For example, referring to FIG. 3 an infrared absorbance spectrum 60 acquired from a sub-sample of the butyl O-ring outgassing products is shown. The strong absorption feature 62 that occurs between 1100 and 1200 $(\text{cm}^{-1})$ is analyzed using gas chromatography-mass spectrometry, for example, and the dominant species in the material is identified as perflouro moiety.

Figure 4:
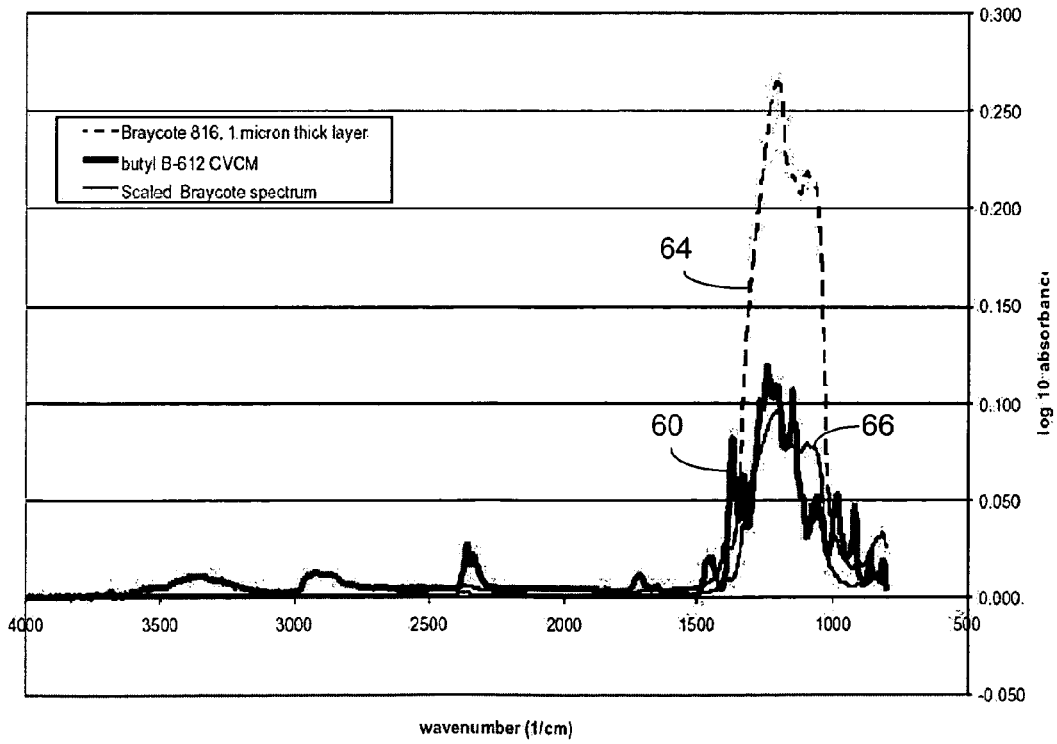
FIG. 4 is an infrared spectrum of the outgassed products of Butyl rubber shown in FIG. 3, along with an absorbance spectrum of a 1.0 micron layer of Braycote 816 and a Braycote vector scaled by a factor of 0.36 in accordance with an embodiment of the present invention.

Next, a pure material is identified that exhibits similar characteristics as the identified dominant species. For example, Braycote 816, which is a perfluorinated oil, can be used as a vector for perfluorinated materials. Referring to FIG. 4, the absorbance spectrum 60 of outgassing products from butyl O-rings is overlaid with the absorbance spectrum 64 of a 1.0 micron thick layer of Braycote 816. A Braycote vector 66, scaled by a factor of 0.36, also is shown in FIG. 4. As can be seen in FIG. 4, the spectral character of the outgassing products of butyl O-rings is similar to the scaled Braycote 816 vector spectrum, particularly in the energy range from 1000 to 1400 $(\text{cm}^{-1})$.

The agreement between the scaled vector 66 and the observed spectrum 60 of solid outgassing products suggests that the outgassing products can be represented by a 0.36 micron layer of Braycote 816 or that the spectrum of observed outgassing products has a thickness equivalent to 0.36 microns of liquid perfluorinated oil.

Dividing the spectrum 60 of outgassing products by the scale factor applied to the scaled Braycote 816 spectrum 66, a vector spectrum of outgassing products that has an equivalent thickness of 1.0 micron is obtained.

Accordingly, the absorbance spectrum of a Type 2 soil can be obtained by selecting a material that has an absorbance spectrum with similar characteristics as the absorbance spectrum of the soil sample. A scaling factor that provides a good fit of the selected material absorbance spectrum with the soil sample absorbance spectrum is determined. Using this scaling factor, the absorbance spectrum of the sample soil can be scaled to provide an absorbance spectrum of a 1.0 micron thick layer of the soil sample.

Type 3—The Outgassing Products are not a Pure Substance and cannot be Represented by a Single Model Compound that is a Liquid The third Type of soil is a contaminant wherein the outgassing products are not a pure substance and cannot be represented by a single model compound that is a liquid. An example of such a contaminant is the outgassing product of Uralane 5753.

As will be described in more detail below, a primary objective in analyzing a Type 3 soil is to obtain a synthetic spectrum of the soil from which an equivalent thickness of the soil can be estimated. The synthetic spectrum is derived by combining model compounds having a 1.0 micron thickness and assigning a scaling factor to each model compound such that the synthetic spectrum forms an approximation of the soil spectrum. Corrections, if necessary, are made to the synthetic spectrum to account for erroneous data, e.g., excessive signals introduced with each vector. The equivalent thickness of the soil sample is estimated by adding the thickness of each scaled model vector of the synthetic spectrum, and adding or subtracting any corrections made to the synthetic spectrum.

Before fitting the soil spectrum, it is preferable that multiple spectra are collected of the soil sample and an average sample spectrum is prepared from the multiple spectra. Additionally, the average sample spectrum should be corrected for reflection losses and atmospheric carbon dioxide, as is conventional.

For example, atmospheric carbon dioxide doublets can be corrected by replacing the data in the region of the doublet with a straight line defined by a baseline on either side of the doublet, for example. Corrections can be performed in the absorbance mode or in the transmittance mode. To avoid having negative values in the absorbency spectrum, no part of the spectrum should exceed 100% transmittance.

Figures 5, 6:
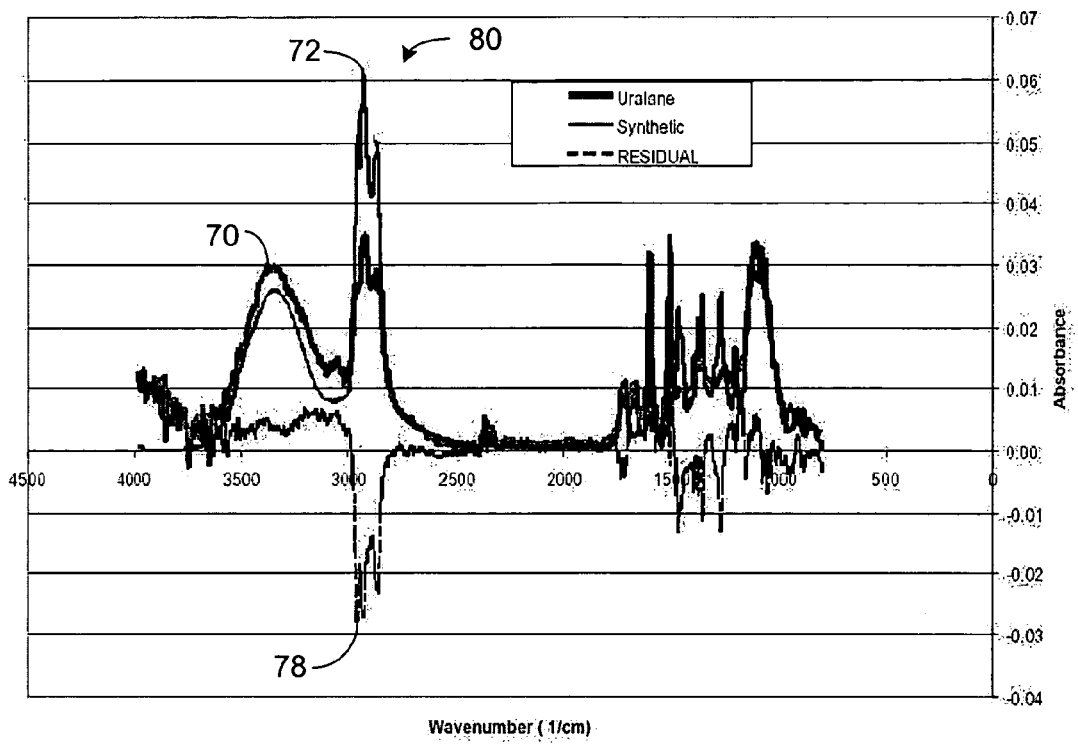
FIG. 5 is an infrared spectrum of outgassed products obtained from Uralene 5753 and a synthetic spectrum obtained using a mix of vector spectra in accordance with an embodiment of the present invention.
FIG. 6 is a table of vector components used to construct the synthetic spectrum of FIG. 5 along with the corresponding thickness assigned to each vector.

Referring to FIG. 5, an absorbance spectrum 70 acquired from the outgassing products collected from Uralane 5753 adhesive is illustrated. FIG. 5 also shows a synthetic spectrum 72 that was produced using vector spectra of several model compounds, and the residual amount 78, or error, that is produced when the synthetic spectrum 72 is subtracted from the sample spectrum 70.

With further reference to FIG. 6, a table of the individual vectors 74 (vector basis set) used to construct the synthetic spectrum and their respective thickness 76 (scalar factors) are shown.

The synthetic spectrum 72 is created by combining normalized vectors for known model compounds to form a spectrum that approximates the sample spectrum 70. Each vector is assigned a thickness 76, which operates as a scaling factor for the particular vector 74. The selection of the vectors 74 making up the synthetic spectrum 72 is based upon knowledge of infrared spectroscopy and chemistry. As will be appreciated by those skilled in the art, different portions of the spectrum clearly are associated with functional groups or chromophores. Selection of compounds for the synthetic spectrum 72 can be based on the absorbance properties of the functional groups within the regions of interest.

The synthetic spectrum 72 is fit to the sample spectrum 70 by manipulating the individual vectors 74 in the synthetic spectrum 72 along with each thickness 76 as necessary (see e.g., FIG. 6). It is noted that the fit of the synthetic spectrum 72 to the sample spectrum 70 need not be perfect, but only provide an accurate approximation of the sample spectrum. The permissible amount of deviation between the measured spectrum and the synthetic spectrum depends on the desired accuracy of the final result. Upon obtaining a good fit of the sample spectrum 70, a first estimate of the equivalent thickness of the soil is calculated. The estimate of the soil sample thickness is calculated by summing the thickness 76 of each individual vector used to create the synthetic spectrum 72. Referring to FIG. 6, the first estimate of the equivalent thickness 79 is the sum of each vector spectra, or 1.15 microns.

The synthetic spectrum 72 can be corrected after the initial fitting. For example, certain areas of the synthetic spectrum 72 may show large deviations from the sample spectrum 70. This is indicated by a residue 78 that significantly deviates from an absorbance of zero. Again, what constitutes a significant deviation depends on the desired accuracy of the final result.

Deviations, for example, can be caused by the sum of all selected vectors overestimating the contribution of certain bands. A positive residue 78 indicates that the synthetic spectrum 72 has an absorbance that is less than the sample spectrum 70 (e.g., it underestimates the sample spectrum), while a negative residue indicates the synthetic spectrum 72 has an absorbance that exceeds the sample spectrum 70 (e.g., it overestimates the sample spectrum).

An overestimate region 80 of the synthetic spectrum 72 illustrates the latter case, wherein the synthetic spectrum absorbance exceeds the sample spectrum absorbance. The overestimate region 80 in the present example is associated with C—H bending motions. The sum of all vectors chosen to create the synthetic spectrum 72 overestimates the contributions from the C—H bands because most of the models chosen for the synthetic spectrum 72 have long aliphatic chains. The overestimate can be corrected by subtracting the CH bands using a simple aliphatic hydrocarbon, such as n-nonane, for example.

To obtain a second iteration of the equivalent thickness for the synthetic spectrum 72 of FIG. 5, an estimate of the total aliphatic and aromatic hydrocarbon thickness in the soil is performed. Removal of the hydrocarbon contribution results in a better approximation of the equivalent thickness. The total aliphatic and hydrocarbon thickness is estimated by trying different thickness levels of a correction compound and observing the results on the synthetic spectrum. The over-subtraction of the C—H bends can be minimized, for example, by subtracting 0.5 microns of n-nonane, as indicated by the flatter residual spectrum under the peaks 82 of FIG. 7. The next approximation for the equivalent film thickness is 0.65 microns, which is obtained by subtracting the thickness of the correction compound, e.g., 0.5 microns of n-nonane, from the first estimate of the thickness 79, e.g., 1.15 microns. The thickness of the correction compound is subtracted from the estimated thickness because the synthetic spectrum 72 overestimates the sample spectrum 70 in the region 80 as evidenced by the negative residue 78. It will be appreciated that if the initial synthetic spectrum 72 resulted in a positive residue 78, then the thickness of the correction compound would be added to the initial estimated thickness 79.

Figures 7, 8:
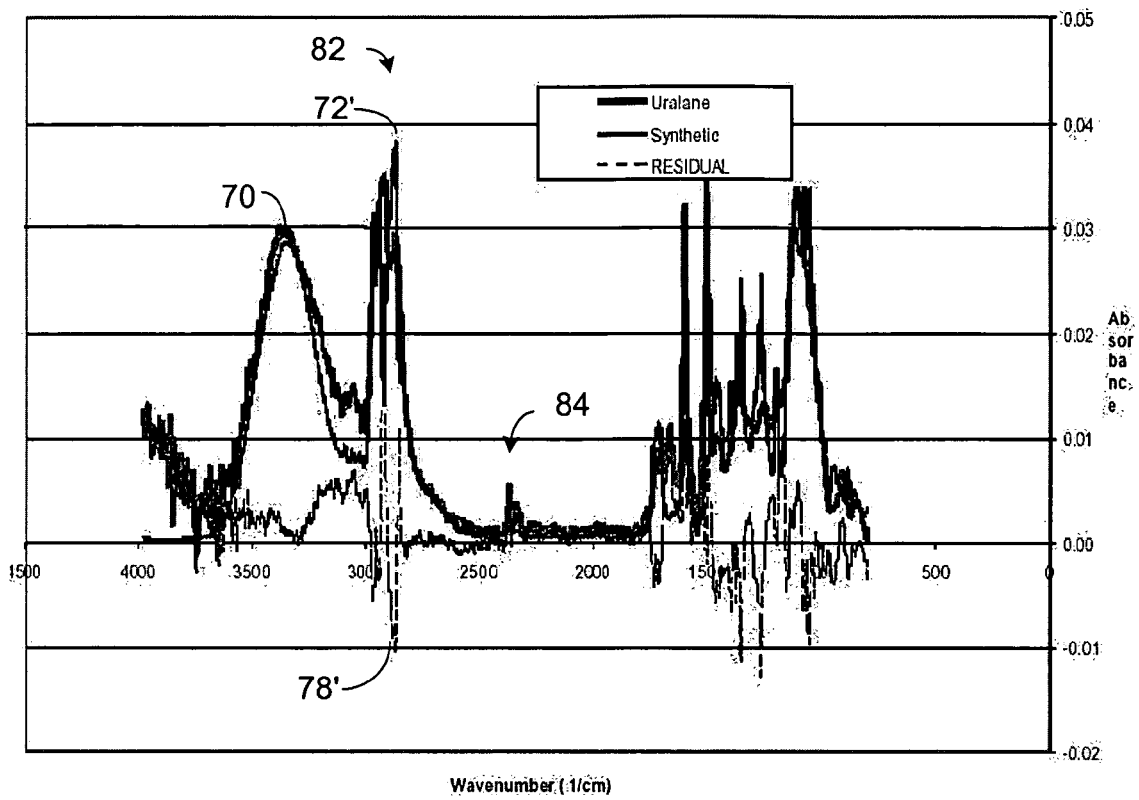
FIG. 7 is an infrared spectrum illustrating the effects of a modification of the synthetic spectrum of FIG. 5 in accordance with an embodiment of the present invention.
FIG. 8 is a table of vector components used to construct the synthetic spectrum of FIG. 7 along with the corresponding thickness assigned to each vector.

The effects of the correction are shown in FIG. 7. The small peak 84 near 2400 (cm$^{-1}$) is an atmospheric carbon dioxide doublet and should be removed prior to creating a vector spectrum. FIG. 8 lists the component vectors 74' and thickness 76' used to produce the estimate. FIG. 8 also lists the known density 86 of the pure compounds used to create the vectors, and the product of the density weighted thickness 88, which is calculated using Equation 6, as is discussed below.

$$A = n \cdot \frac{\sum_i p_i t_i}{\sum_i p_i}$$ Equation 6

$$B = \frac{\sum_i p_i t_i}{\sum_i t_i}$$ Equation 7

An improved estimate of the thickness can be obtained by weighting the thickness of each compound by the density of the compound. This process is defined by Equation 6, where $p_i$ is defined as the density of the CVCM component i in grams per cubic centimeter, $t_i$ is defined as the thickness of the CVCM component i in microns, i is the index of components to fit, n is the number of components and A is defined as the density weighted thickness in grams per cubic centimeter. For example, each thickness 76' is multiplied by the density 86 of the respective component to arrive at a density weighted thickness 88 for each particular vector. Each density weighted thickness 88 then is summed together to arrive at a total density weighted thickness 88'. The total density weighted thickness 88' is divided by the total summed density 86', and the result is multiplied by the number of vectors used to create the synthetic spectrum 72'. The result is a new estimate of the equivalent thickness 79".

Equation 7 defines an equivalent average density for the aggregate soil, where B is defined as the average thickness weighted density in grams per cubic centimeter. Equation 7 is used to calculate an approximate density for the soil. The approximate density is used to convert a contaminant's mass into volume.

Accordingly, an absorbance spectrum per unit thickness is obtained by dividing the measured absorbance spectrum 70 of the soil sample by the estimated soil sample thickness 79', 79", as was described above with regards to a Type 2 soil.

The pure liquids chosen to represent a given chromophore generally will have fewer functional groups than a typical outgassing soil. An assumption of the present analysis is that the molar volume of a soil is similar to the molar volume of the pure liquids. While this assumption is flawed, it permits the assignment of an equivalent thickness to a spectrum, so that the contribution of a given substance to the aggregate soil and the effect of that aggregate soil on the optical performance of a sensor can be estimated.

It is noted that basing an estimate of the equivalent film thickness on a spectral fit requires some judgment and a fair amount of chemical intuition. Generally, this process should not be automated in such a way that the weighting factors from the spectral fit automatically define the equivalent thickness. A good understanding of chemistry, material composition and infrared spectroscopy are necessary. Additionally, the synthetic spectrum 72 generally is not a perfect fit, and sharp spikes can be produced from small wavelength shifts in the position of the band for each functional group. These wavelength shifts depend on the structure of the backbone to which the functional group is attached.

As stated previously, the choice of vectors to apply to the synthetic spectrum is highly subjective. Material Safety Data Sheets (MSDS) can be used to aid in vector selection. For example, the choice of polyethylene glycol as a vector for the fit of Uralane 5753 was based on the information in the MSDS. Similarly, the choice of N,N-diethyl aniline as a vector was based on the use of a chemically similar material in the adhesive.

In some instances, information may not be readily available for a specific material or the spectral character of the soil differs from pre-test expectations. In such circumstances, a list of chromophores and their typical wavelength ranges may be useful.

Figure 9:
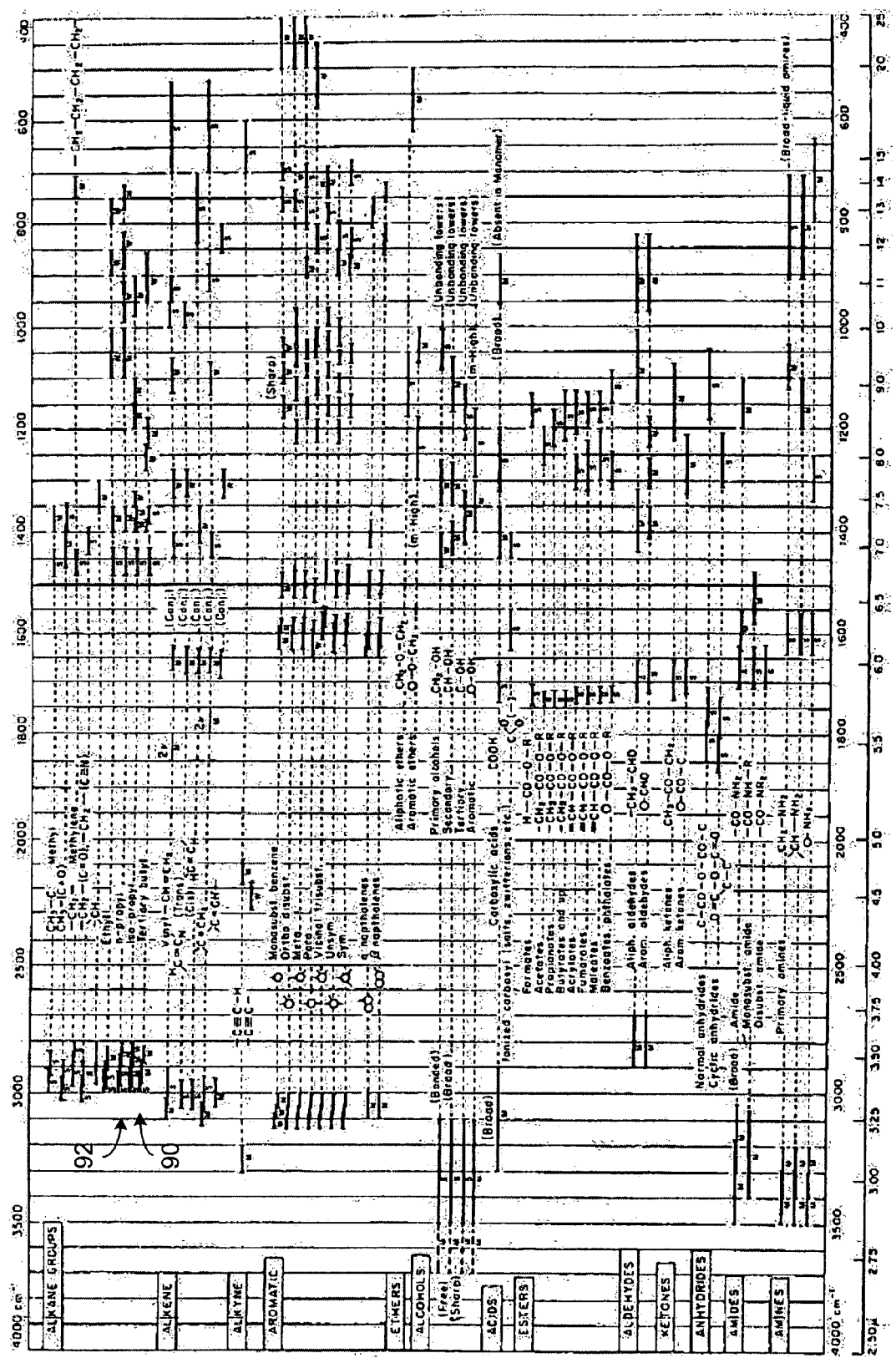
FIG. 9 is a map of functional groups and their typical wavelength ranges.

For example, a high absorbance may be desired in the 3000 ($cm^{-1}$) range. Referring to the characteristic infrared group frequencies map of FIG. 9, groups having the desired strength of absorption bands in the 3000 ($cm^{-1}$) range are identified. As is conventional, strong absorption bands are indicated with an "S", medium absorption bands are indicated with a "M", and weak absorption bands are indicated with a "W". Tertiary butyl 90 and n-propyl 92, for example, exhibit strong absorption in the 3000 ($cm^{-1}$) range, and thus each can be used as a component vector for the synthetic spectrum to achieve a desired result in the range of interest.

Alternate analytical techniques, such as mass spectrometry, for example, can aid in identifying the presence of moieties. Additionally, new model compounds can be used to make vector spectra for fitting the spectra of soils.

While a perfect fit is desired, it is unlikely that one will be attained. One should not be too concerned with fitting C—H bands near 3000 ($cm^{-1}$) at first, except to capture the aliphatic and aromatic character. The fit of prominent spectral features should be prioritized, with more weight given to chromophores known to be strong absorbers, such as silicones or carbonyl groups, for example. Broad OH and NH features above 3000 ($cm^{-1}$) are useful fiducials for the CO and CN bands that occur between 1600 ($cm^{-1}$). In particular, these features are useful for selection of vectors and as aids to fine tune the thickness of different vector components.

The vector spectra created by the methods described herein are intended to be the basis set for predicting the infrared spectrum of an aggregate outgassing soil. The thickness of the aggregate soil is estimated using the mass fraction of volatile soils collected on a cold plate during an accelerated outgassing test (ASTM E595). It is important to separate the uncertainty associated with the knowledge of the CVCM from the uncertainty associated with the equivalent thickness estimate applied to the spectrum of the CVCM soil. The following discussion is restricted to the uncertainties in assigning the equivalent thickness of a given CVCM spectrum.

The uncertainty associated with the equivalent thickness of each vector spectrum is unique to the each vector. Clearly a vector created from a model compound has a low uncertainty, generally being on the order of 5% to 10% Relative Standard Deviation (RSD). The uncertainty associated with other vectors may range from 10% to 100% RSD. It is the inventors' opinion that the general range of uncertainty for the applied equivalent thickness is on the order of 20% to 50%.

The quantity of soils collected from an outgassing test generally is quite small, with a total mass on the order of 0.1 to 2 milligrams. This material usually is deposited over a 1 centimeter diameter area as a non-uniform distribution of droplets, films and crystals. The distribution of material usually is not uniform in composition or physical form. Neighboring droplets can exhibit a vastly different infrared spectra. Therefore, the vector spectra are collected in such a way to provide an average response.

The quantity and type of soils collected may depend on how the material was processed. Processing includes, but is not limited to: outtime prior to cure; shipping and storage conditions of uncured material; mixing ratio; cure schedule; post cure treatment; storage after cure; environment during transport and shipping; and testing conditions.

Accordingly, an absorbance spectrum per unit thickness of a Type 3 soil can be obtained by constructing a synthetic spectrum that approximates the absorbance spectrum of the soil sample. Using scaling factors applied to each vector of the synthetic spectrum, along with any correction factors, an equivalent thickness of the soil sample is estimated. Dividing the measured absorbance spectrum of the soil sample by the estimated thickness produces an absorbance spectrum per unit thickness of the soil sample.

Figure 10A:
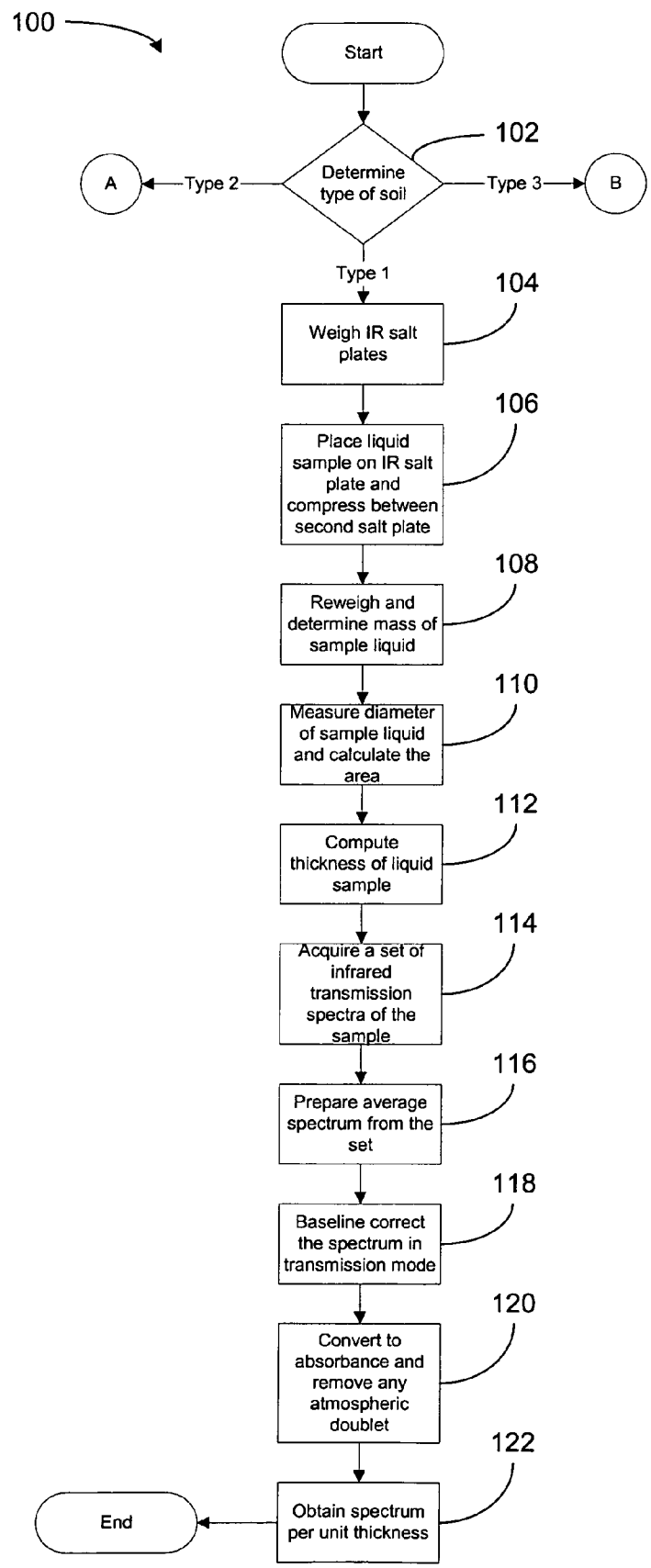
FIG. 10A is a flow diagram illustrating an exemplary method of estimating the equivalent thickness of a soil in accordance with an embodiment of the present invention.
Figure 10B:
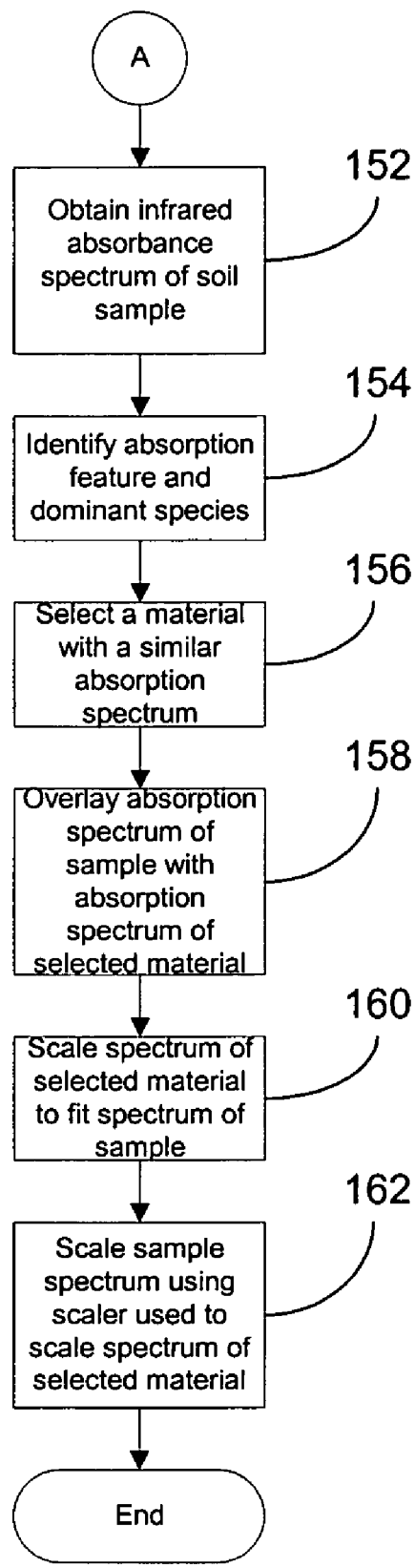
FIG. 10B is a continuation of the flow chart of FIG. 10A.
Figure 10C:
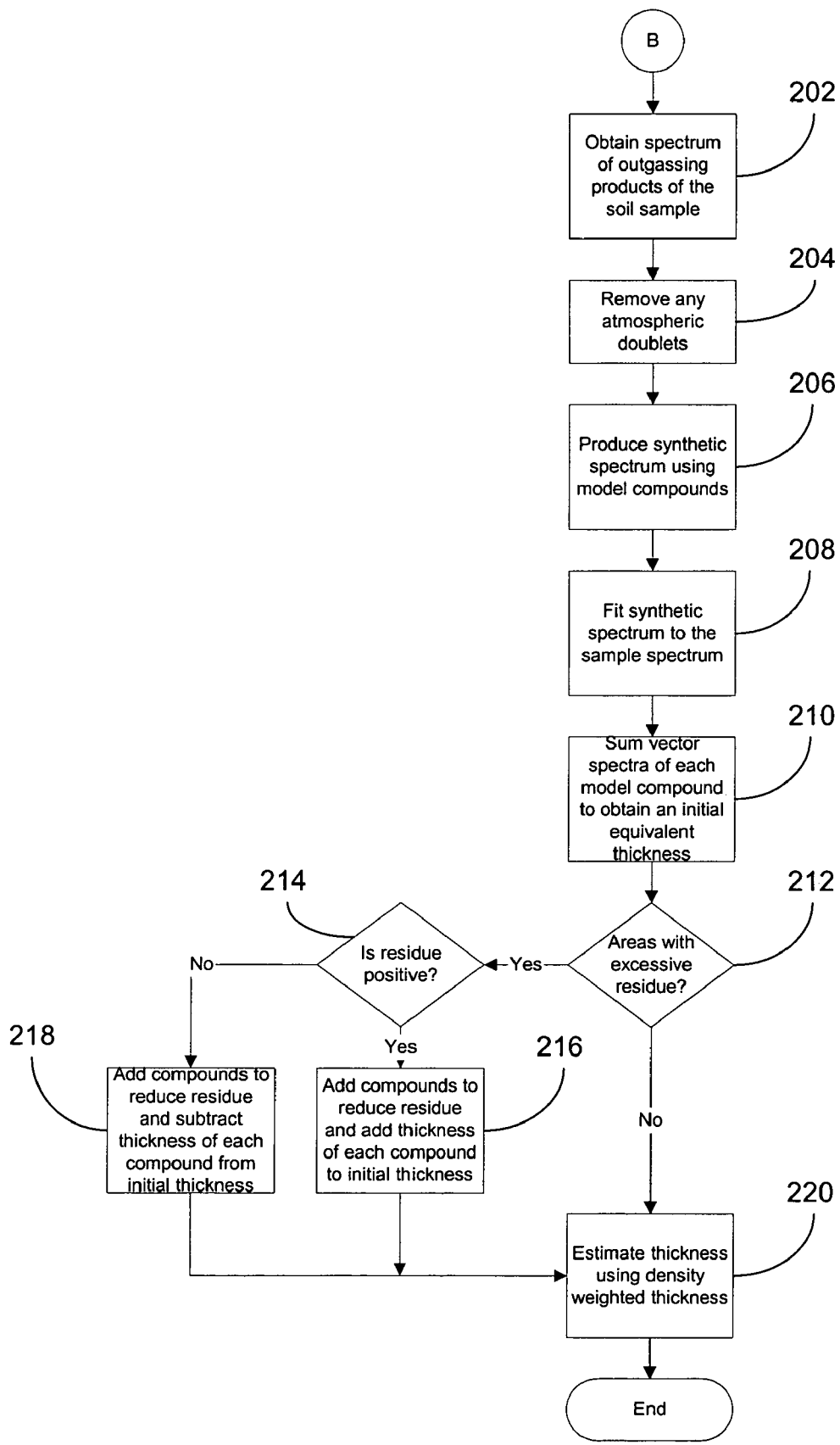
FIG. 10C is a continuation of the flow chart of FIG. 10A.

Referring now to the flowchart 100 of FIGS. 10A-10C, exemplary steps for obtaining an absorbance spectrum per unit thickness of a soil are shown. Beginning at step 102, the soil is classified into one of three different types. The first type of soil is a contaminant that is a pure substance and is in liquid form at room temperature. The second type of soil is a contaminant that is not a liquid or a pure substance, but an infrared spectrum indicates that the absorbance in the region(s) of interest is dominated by a single functional group. Finally, the third type of soil is a contaminant that has outgassing products that are not a pure substance and cannot be represented by a single model compound that is a liquid. If the soil is a Type 1 soil, then at step 104, two IR salt plates are weighed, preferably to the nearest 0.01 milligram. At step 106, a liquid sample of the soil is placed on one of the IR salt plates, and the second IR salt plate is placed over the first IR salt plate. The liquid sample is compressed between the two IR salt plates to about two centimeters in diameter. The combination of the liquid sample and the IR salt plates are weighed at step 208 (again, preferably to the nearest 0.01 milligram), and the mass of the soil sample is calculated. The mass of the soil sample is calculated as the mass of the soil sample and salt plates minus the mass of the salt plates. At step 110, the diameter of the soil sample is measured and the area occupied by the liquid sample is calculated. The area can be calculated assuming the sample is circular and applying Equation 2. If the sample clearly is not circular, e.g., it is elliptical, then two measurements can be made; one of the ellipse's major axis and one of the ellipse's minor axis. Using Equation 3, the area of the soil sample is calculated.

Moving to step 112, the thickness of the soil sample is calculated based on the geometry and the physical properties of the sample. As described previously, the area of the sample is calculated assuming either a circular or elliptical shape and using the measured parameters, e.g., the diameter of the circle or the length of the major and minor axis of the ellipse. Using the calculated area of the sample, the measured mass of the sample, and the density of the sample (measured or known), the thickness of the sample is calculated using Equation 1.

At step 114, a set of infrared spectra of the soil sample are acquired. Preferably, several samples are obtained, and the samples are rotated between each measurement. An average spectrum is obtained from the several samples at step 116, and the spectrum is baseline corrected in transmission mode at step 118. At step 120, the spectrum is converted to absorbance mode and atmospheric doublets are removed from the spectrum. At step 122, the average spectrum is divided by the measured thickness of the soil sample to obtain the absorbance spectrum per unit thickness of the soil.

Accordingly, an absorbance spectrum of the soil sample is obtained. Moreover, the thickness of the soil sample used to obtain the absorbance spectrum is derived. Using the absorbance spectrum and the calculated soil thickness, a per unit absorbance spectrum for the soil is derived.

Moving back to step 102, if the soil is a Type 2 soil, then at step 152 of FIG. 10B, an infrared absorbance spectrum 60 of the soil sample is obtained. At step 154, a strong absorption feature 62 in the absorbance spectrum 60 and a dominant species responsible for the strong absorption feature 62 are identified. Next, at step 156 a material is selected that has an absorbance spectrum that is similar to the absorbance spectrum 60 of the soil sample, and at step 158 the absorbance spectrum 64 of the selected material is overlaid with the absorbance spectrum 60 of the soil sample.

Moving to step 160, the absorbance spectrum 64 of the selected material is scaled to approximate the strength of the absorbance spectrum 60 of the soil sample. Using the scale factor applied to the absorbance spectrum 64 of the selected material, the absorbance spectrum 60 of the soil sample is scaled (e.g., divided by the scale factor applied to the selected spectrum) at step 262 to approximate an absorbance spectrum that would be obtained from a 1.0 micron thick soil sample. Accordingly, an absorbance spectrum per unit thickness of a Type 2 soil is obtained.

Moving back to step 102, if the soil is a Type 3 soil, then at step 202 of FIG. 10C an absorbance spectrum 70 of the outgassing products of the soil sample is obtained and at step 204, any atmospheric carbon dioxide doublet present in the absorbance spectrum is removed. At step 206, a synthetic absorbance spectrum 72 is constructed, wherein the synthetic absorbance spectrum approximates the absorbance spectrum 70 of the outgassing products. As was described previously, the synthetic spectrum 72 is constructed by combining normalized vectors 74 for known model compounds to form a spectrum that approximates the absorbance spectrum 70 of the outgassing products. Each vector is assigned a thickness 76, which operates as a scaling factor for the particular vector 74. The selection of the vectors 74 making up the synthetic spectrum 72 is based upon knowledge of infrared spectroscopy and chemistry.

At step 208, the synthetic spectrum 72 is fit to the spectrum 70 of the outgassing products. Fitting includes manipulating the thickness 76 of each vector 74, and adding or removing model compounds as necessary to achieve a good fit between the synthetic spectrum 72 and the spectrum 70 of outgassing products. When a good fit between the synthetic spectrum 72 and the spectrum 70 of outgassing products is obtained, an estimate of the equivalent thickness of the soil is calculated by adding the thickness 76 assigned to each model vector compound 74 as indicated in step 210. An improved estimate can be obtained by weighting the thickness 76 of each model compound by the density of the compound, as identified previously with respect to Equation 6.

At step 212, the fit between the synthetic spectrum 72 and the spectrum 70 of outgassing products is compared and any excessive residue 78 is identified. If the residue is not excessive, then the process moves to step 220. If residue 78 is excessive, then at step 214 it is determined whether the residue is positive or negative. If the residue is positive, then at step 216 compounds are added to the synthetic spectrum 72 to reduce the residue 78 (i.e., make the residue less positive), and the thickness of each added compound is added to the initial estimate of the equivalent thickness of the soil. If, on the other hand, the residue 78 is negative, then at step 218 compounds are added to the synthetic spectrum 72 to increase the residue 78 (i.e., make the residue less negative), and the thickness of each added compound is subtracted from the initial estimate of the equivalent thickness of the soil. At step 220, an improved estimate can be calculated using the density weighted thickness, as was described with respect to Equation 6.

Accordingly, an embodiment of a method for estimating an absorbance spectrum per unit thickness of a soil sample has been disclosed. In a second embodiment, the method of estimating an absorbance spectrum per unit thickness is used to estimate the degradation in performance of a sensor due to outgassing of soils.

Figure 11:
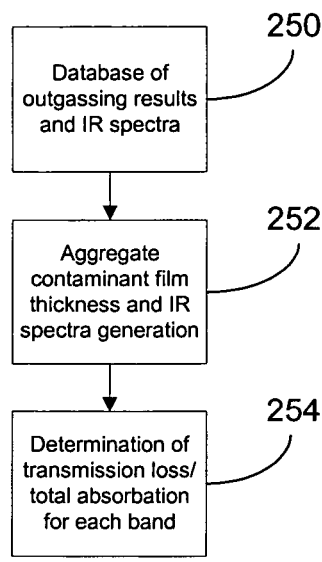
FIG. 11 is a block diagram illustrating a first, second and third module used to estimate the effect of a contaminant film on the performance of a sensor in accordance with another embodiment of the present invention.

Moving to FIG. 11, a simple block diagram illustrating three software modules used to implement another embodiment of the present invention is shown. It should be appreciated that while the block diagram illustrates three separate modules, the modules can be combined into more or less modules without departing from the scope of the invention. The present embodiment estimates the equivalent soil thickness that can be produced from outgassing products for each component within the sensor. An aggregate soil spectrum is constructed from the individual outgassing products, and the effect of the aggregate film on sensor performance is estimated.

A first module 250 stores data of outgassing results and spectra for various compounds, and fits acquired CVCM spectra with a set of vector spectra that have known absorbance values and per unit layer thicknesses. The data stored in the first module 250 is used by a second module 252, along with specific information relating to an object of interest, e.g., a sensor, to calculate a total aggregate contaminant film thickness that can accumulate within the sensor. Additionally, the second module generates a spectrum of the aggregate contaminant film. A third module 254 determines the transmission loss and total absorption that would occur in the sensor due to the aggregate contaminant film generated by the second module 252.

Figure 12:
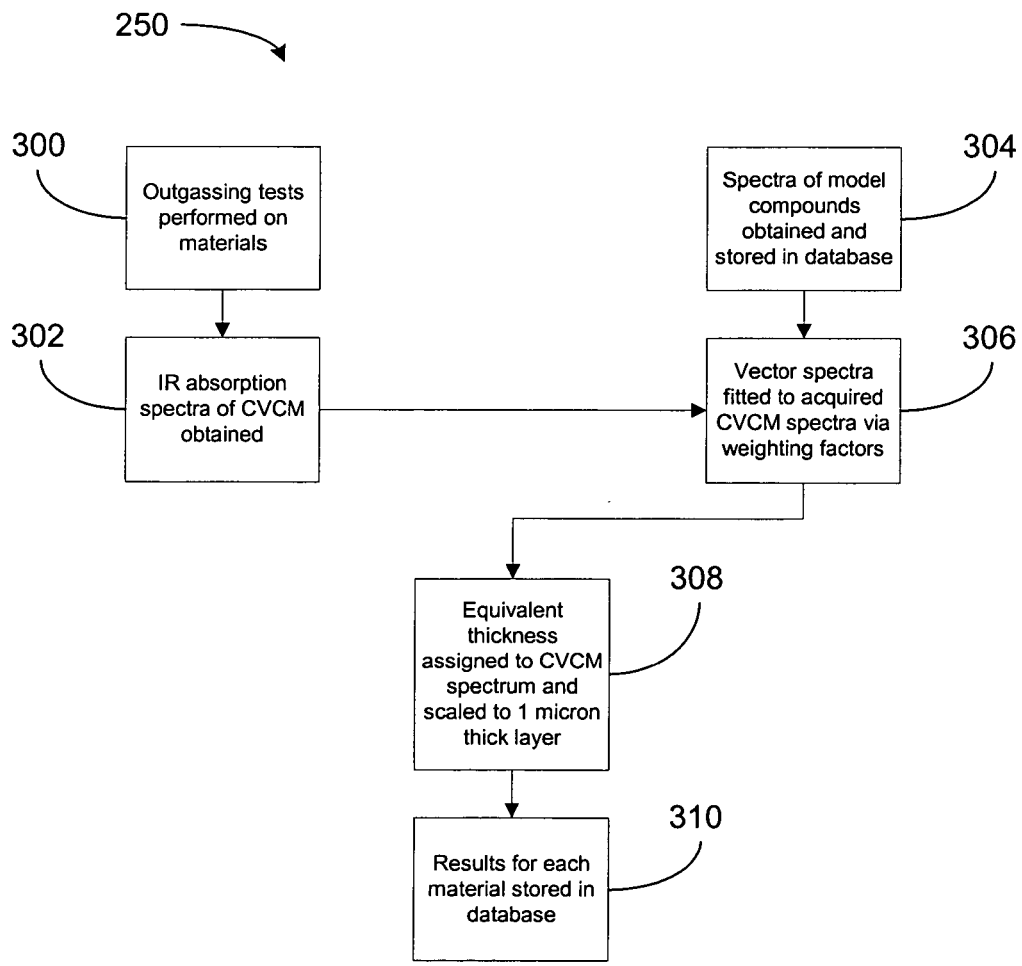
FIG. 12 is a flow chart illustrating exemplary steps performed in the first module of FIG. 11.

Referring to the flowchart of FIG. 12, exemplary steps performed by the first module 250 are illustrated. As was briefly stated above, the first module stores data of outgassing results and spectra for various known compounds. Additionally, the first module approximates the thickness of a sample of outgassed soil used to obtain an absorbance spectrum. The first module produces a normalized spectrum of the soil sample. Beginning at step 300, the materials typically used to construct the sensor are determined, e.g., rubber, plastic, vinyl, etc., and outgassing tests are performed on the materials. The results of the tests are entered into the first module 250.

For example, outgassing soils are collected from a sample of each material using a modified form of the ASTM E595 test for CVCM of outgassed soils. The ASTM E595 test is well known in the art and will not be discussed in detail herein. A modified form of the ASTM E595 test is used to provide improved estimates of the CVCM load as compared to the standard test. The standard ASTM E595 test tends to underestimate the maximum load of CVCM by about a factor of 2. The modified test employed herein compensates for this inaccuracy by performing the test for a longer period of time (48 hours as opposed to 24 hours). Additionally, the modified test is conducted at ambient pressures (the ASTM E595 procedure is performed in a vacuum), and mass data are corrected to mass in vacuo to correct for errors resulting from air buoyancy. Furthermore, a sample compartment used for holding the sample is enlarged to hold several grams of the sample, and the distance between a sample chamber and a collector plate is decreased by a factor of 2. Preferably, the CVCM is collected on a highly polished aluminum coupon. It also is preferable that a large sample (e.g., about 1 gram) is used in order to obtain a measurable mass of CVCM.

If it is not feasible to perform the above modified form of the ASTM E595 test or published ASTM E595 results are used, it is prudent to increase the E595 data by a factor of 2 when estimating the maximum load CVCM in a material.

As shown in step 302, infrared absorption spectra of a sample of each outgassed soil are acquired. The infrared spectra can be acquired from the sample by low angle reflectance on a Fourier transform spectrophotometer. A large aperture is used to obtain an optical average of the collected material. Preferably, five spectra are acquired and an average spectrum is computed. Background data is subtracted using conventional techniques.

In step 304, spectra of known model compounds are normalized to a unit thickness and stored in a database of the first module 250. Ideally, the spectra of known model compounds entered into the database would include all possible components that relate to the sensor. Since this may not be practical, it is preferable that the model compounds entered into the database provide the basic compounds commonly encountered in one's process. If the spectra of model compounds in the database are not sufficient to create an accurate synthetic spectrum, then additional spectra can be entered at a later time to accommodate future needs.

In step 306, a vector spectrum is fit to the acquired soil spectrum. Depending on the type of soil, the vector spectrum may be fit in one of several ways as was described previously. For example, if the soil is a Type 1 soil, e.g., the contaminant is a pure liquid, then the spectrum can be measured and the thickness can be calculated using Equations 1-3. If the soil is a Type 2 soil, e.g., the contaminant is not a liquid or a pure substance but an infrared spectrum indicates that the absorbance in the region(s) of interest is dominated by a single functional group, then the spectrum can be represented by a single pure liquid, and a measured spectrum of the soil is scaled based on a scalar applied to the spectrum of the pure liquid. If the soil is a Type 3 soil, e.g., the contaminant is not a pure substance and cannot be represented by a single pure liquid, then the spectrum is represented by a linear combination of pure liquids.

An equivalent thickness is assigned to the soil at step 308, and the spectrum is scaled or normalized to represent a spectrum of a 1.0 micron thick layer of the soil sample. The normalized spectrum is used as a vector in the second module 252, as will be discussed below. The derivation of the equivalent thickness and the spectrum is determined based on the type of soil (e.g., Type 1, 2, or 3), as was discussed previously. The equivalent thickness and normalized spectrum are stored in the database of the first module 250, as indicated at step 310.

Figure 13:
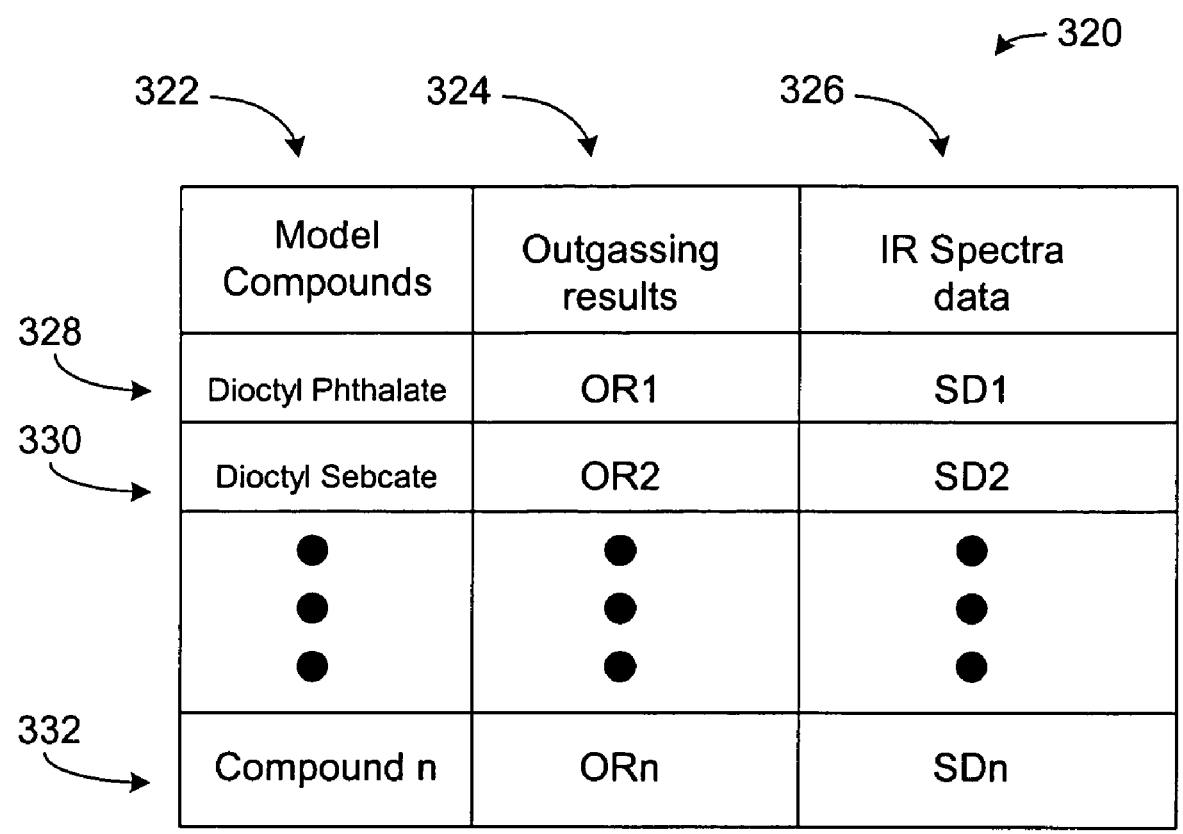
FIG. 13 is an exemplary database structure used to store outgassing data and spectral data of model compounds in accordance with an embodiment of the present invention.

Referring to FIG. 13, an exemplary database structure 320 that can be used to construct the database of the first module 250 is illustrated. The database structure 320 includes a model compound entry 322, which is a listing of model compounds that may be used to model the outgassed soils from the sensor. An outgassing results entry 324 stores the results of outgassing tests performed on each model compound, and an IR spectra data entry 326 stores the data pertaining to a measured spectrum of a 1.0 micron thick layer of each model compound.

Each model compound is entered into the database along with its respective outgassing results and IR spectra data in the above described entries. For example, a first model compound may be Dioctyl Phthalate, and is entered in a first row 328 of the database. Corresponding outgassing results and spectral data for Dioctyl Phthalate also are stored in the first row under the respective columns. A second model compound may be Dioctyl Sebcate, and is entered in a second row 330 of the database, along with its corresponding outgassing results and spectral data. As stated previously, compounds are entered into the database as needed to fit the soils typically encountered in the sensor.

The second module 252 uses the information stored in the first module 250 (e.g., the normalized spectra) along with additional information relating to the sensor (e.g., the materials used to construct the sensor and their respective mass, and the surface area available for contamination) to construct an aggregate contaminant film spectrum. Additionally, the second module 252 calculates the worst case thickness of a contaminant film that can be formed within the sensor.

As will be discussed below, each pertinent material in the sensor is selected and its mass is entered into the second module. For each material, the mass of the material is multiplied by the CVCM value (i.e., the ratio of the mass of outgassing soil collected from a sample divided by the initial mass of the sample) to give the total mass of the contaminant. Dividing the soil density (approximate) and the surface area available for contamination into each contaminant mass (see, e.g., Equation 1) results in the individual thickness for each particular contaminant. The linear combination of each contaminant thicknesses gives the aggregate film thickness.

The IR absorbance spectrum of the aggregate film is approximated by first multiplying the soil vector spectrum for each contaminant by the thickness of the respective contaminant. The resulting spectrum is a contaminant vector spectrum and represents an absorbance spectrum for a contaminant having the designated thickness. The linear combination of contaminant vector spectra from each pertinent material gives the IR absorbance spectrum of the aggregate film.

Figure 14:
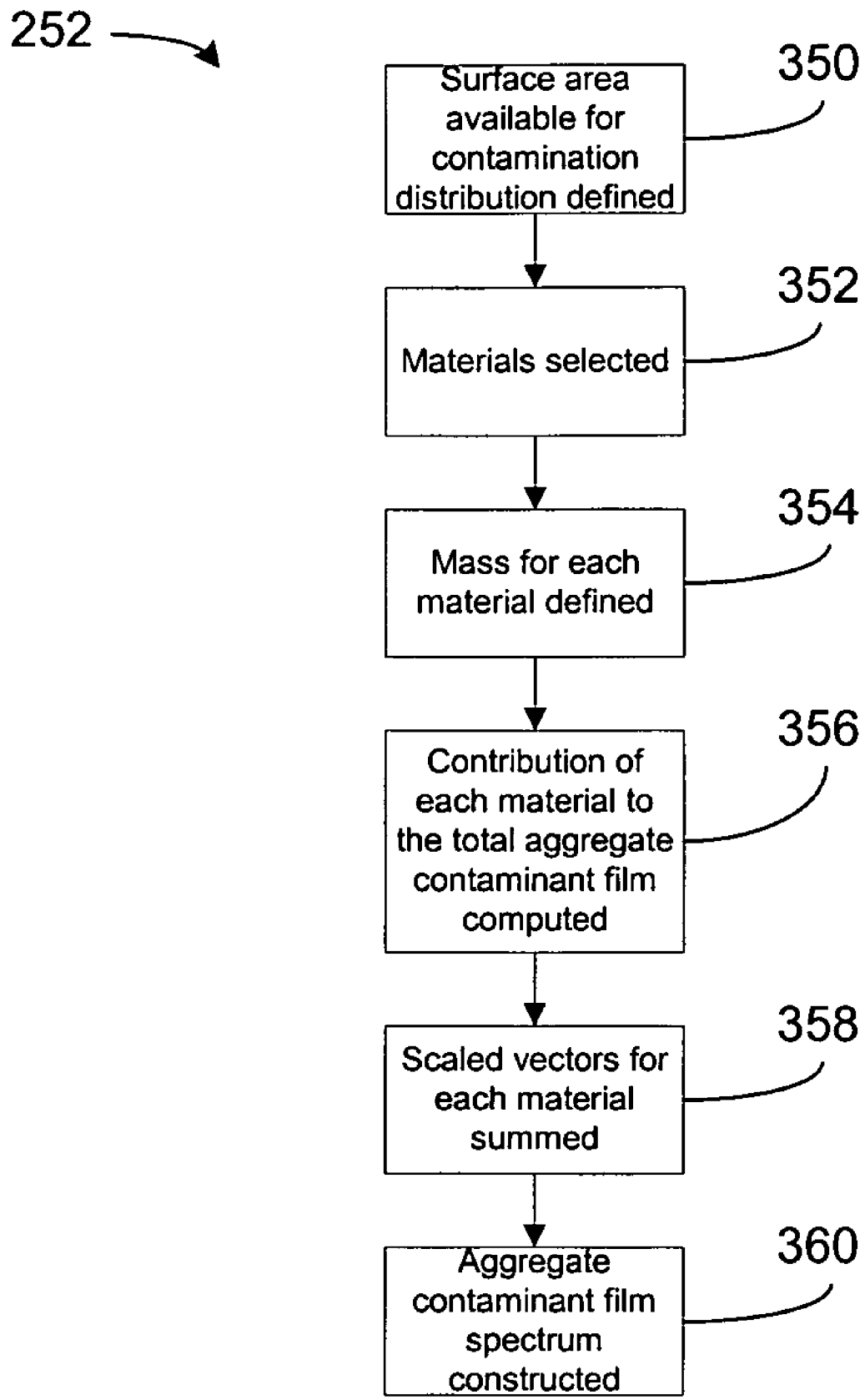
FIG. 14 is a flow chart illustrating exemplary steps performed in the second module of FIG. 11.

Referring to FIG. 14, a flow chart illustrating exemplary steps performed in the second module 252 is shown. Beginning at step 350, the surface area available for contamination is entered into the second module. For example, the surface area of a lens or mirror that will be exposed to the contaminant is calculated, and the calculated area is entered into the second module. At step 352, materials used to construct the sensor are selected. For example, various components are used to construct a sensor, some of which create contamination through outgassing. Generally, the materials used to construct the sensor can vary depending on the purpose and performance goals of the sensor. A first sensor may use a particular type of paint that is different from the paint used in another sensor. Different types of rubber may be used in creating O-rings for the sensor, and/or different types of plastic may be used for components within the sensor. Each of these materials is selected, for example, via drop down menus in the second module. The drop down menus can include, for example, a material category, class and vector selection menus.

Upon selection of each material, the mass of each material is entered into the second module, as shown at step 354. Preferably, the mass of each material is entered to the nearest 0.01 milligram. Upon entry of all materials used in the sensor and the corresponding mass of each material, the second module 252 calculates the thickness contribution of each material to the total aggregate contaminant film, as shown at step 356. The thickness contribution of each material to the total contaminant film is calculated by dividing the estimated volume of soil from a respective material by the total internal surface area of the sensor, or in other words, by dividing the density of each soil and the surface area in the sensor available for contamination into the mass of the respective soil (Equation 1).

The second module 252 uses the thickness contribution of each material as a scalar multiplier for the vector spectrum derived in the first module 250. For example, based on the materials chosen in the drop down menu of the second module 252, the second module retrieves the normalized spectrum for each selected material from the first module 250. Upon retrieval of each spectrum, the second module scales (e.g., multiplies) each spectrum by its respective calculated thickness contribution.

At step 358, an equivalent thickness of the aggregate soil is calculated by adding the calculated thickness contribution for each soil component (i.e., CVCM from each material) of the sensor. An aggregate soil spectrum is constructed by summing the scaled vectors for each soil component of the sensor, as shown at step 360.

FIG. 15 illustrates exemplary calculations for estimating film thickness from outgassing data. The surface area used in the calculations of FIG. 12 is 0.8 (m$^2$). Outgassing products from an adhesive and polymer are considered along with a generic non-volatile residue (NVR) soil from piece parts. The Volume of Material 370 (cm$^3$) is estimated based on knowledge of the particular components used in constructing the sensor. For example, an O-ring used in the sensor is known to have a certain inner and outer diameter, as well as a particular thickness. Based on this information, the volume of the O-ring can be calculated. Similarly, the Density of Material 372 (g/cm$^3$) is known based on the properties of the components used in the sensor. For example, Butyl rubber is used to make an O-ring in the sensor. Therefore, the density of Butyl rubber is known or can be measured. The CVCM of Material 374 (% m/m) and the Density of CVCM 376 (g/cm$^3$) are retrieved by the second module 252 from the first module 250 based on the selected materials used in the sensor. The Estimated Volume of CVCM 378 (cm$^3$) is obtained from Equation 8, where V is the Volume of material 370, D1 is the Density of Material 372, C is the CVCM of material 374, and D2 is the Density of CVCM 376. The Estimated Thickness of CVCM 380 (nm) is calculated by dividing the Estimated Volume of CVCM 378 by the surface area available for contamination (e.g., 0.8 m$^2$).

$$\text{Estimated Volume} = \frac{V \cdot D1 \cdot C}{D2} \qquad \text{Equation 8}$$

Referring to FIG. 16, the spectral characteristics for each soil listed in FIG. 15 are illustrated. The spectral characteristics are weighted by the final thickness expected from each soil. The spectra of the individual components are offset from zero for clarity. Due to the linear relationship between absorbance and pathlength (shown in Equation 11 below), the estimated absorbance spectrum of the combined soil can be prepared by summing the component spectra.

The third module 254 determines the maximum transmission loss of the sensor due to molecular film contamination from outgassing of components. The transmission loss is based on the estimated absorption spectra and thickness of the molecular film as estimated by the second module 252 convolved with the instrument function of the sensor. The thickness value determined by the second module 252 is applied to all optical surfaces of the sensor to determine the total optical path of attenuation. The result is an estimate of the worst case transmission loss that the sensor could experience due to the presence of molecular film contamination from outgassing.

Optical systems generally employ sensors that are photometers with broad band pass filters. The sensors observe objects that are low temperature, blackbody radiators. The observed signal, for a given target, is an integrated response to the radiation over the entire band pass of each sensor. Films can degrade performance by attenuation of light, scattering of light and increased emissivity.

$$\text{transmittance} = \frac{I(\lambda, T)}{I_0(\lambda, T)} \qquad \text{Equation 9}$$

Depending on the type of sensor and its intended function, one or more detectors are employed within the sensor. For example, a hypothetical sensor may use two detectors, IR1 and IR2. The transmittance of channels IR1 and IR2 are primary metrics for sensor degradation from films. Transmittance is defined by Equation 9, where $I(\lambda,T)$ is the incident intensity (W/cm$^2$) at a given wavelength and temperature, and $I_0(\lambda,T)$ is the transmitted intensity (W/cm$^2$) at a given wavelength and temperature. The transmittance through IR1 relative to the transmittance through IR2 is another important metric for sensor performance. The ratio IR1/IR2 is referred to as the relative band transmittance.

It is well known that the attenuation of light is proportional to the thickness of the film, the absorbing power of the film and the intensity of the radiation. This relationship is described by Equations 9-12, where $I(\lambda)$ is the average attenuated intensity in interval $d\lambda$ (W cm$^{-2}$ μm$^{-1}$), $I_0(\lambda)$ is the average incident intensity in interval $d\lambda$ (W cm$^{-2}$ μm$^{-1}$), $\alpha(\lambda)$ is the absorption coefficient (cm$^3$ mole$^{-1}$ cm$^{-1}$), $\beta$ is the path length (cm), $\gamma$ is the concentration (mole cm$^3$), and $\chi(\lambda)$ is the modified absorption coefficient (cm$^{-1}$). Equation 11 permits the absorbing power of the film to be defined without knowing the composition of the film.

$$I(\lambda) = I_0(\lambda) \cdot \exp(-\alpha(\lambda) \cdot \beta \cdot \gamma) \quad \text{Equation 10}$$

$$I(\lambda) = I_0(\lambda) \cdot \exp(-\chi(\lambda) \cdot \beta) \quad \text{Equation 11}$$

$$\text{absorbance}(\lambda) = -1 \cdot \ln\left(\frac{I(\lambda)}{I_0(\lambda)}\right) = \chi(\lambda) \cdot \beta \quad \text{Equation 12}$$

$$\int_{\lambda_1}^{\lambda_i} \chi(\lambda) \cdot \beta \cdot d\lambda = -1\ln\left(\frac{\int_{\lambda_1}^{\lambda_2} I(\lambda_1 T_1)}{\int_{\lambda_1}^{\lambda_2} I_0(\lambda_1 T_1)}\right) \quad \text{Equation 13}$$

In order to compute the attenuation of a film, it is important to estimate the thickness ($\beta$) of the accumulated soil layers, but it is equally important to estimate the absorbing power per unit thickness ($\alpha(\lambda)$) of each soil. It is not practical to measure or predict the composition of soils in terms of discrete chemical species. It is practical, however, to measure the absorbance spectrum of collected soils. It is therefore convenient to express the attenuation of light in terms of a modified absorption coefficient $\chi(\lambda)$, which does not require knowledge of the concentration of the species of film present. The remaining challenge is to measure the absorbance spectrum per unit thickness for a given soil, as was discussed above with respect to FIGS. 10A-10C.

The effect of all accumulated soils is a function of the amount of each type of soil present and is computed by convolving (i.e., integrating the absorption loss at each wavelength) the incident intensity with the instrument calibration and absorbance spectrum over the spectral band pass. The total attenuation is computed by integrating the energy over the band pass, as described by Equation 11. The transmittance is obtained by dividing the attenuated signal by a similar quantity computed without attenuation from the film.

The total path length through the film is computed by multiplying the film thickness by the total number of times light traverses the film. Each transmission surface counts as one pass, while each reflective surface counts as two passes. The accumulated soils are assumed to be evenly distributed over all available surfaces at the end of the object's service lifetime and the composition of the film also is assumed to be fixed and uniform. Equation 12 describes the relationship between the absorbance, absorption coefficient and pathlength over small wavelength intervals. Absorbance is proportional to the logarithm of the transmittance. The attenuation of light, in absorbance units, is proportional to the pathlength (film thickness) for a given soil. Equation 13 shows that an absorption coefficient, computed over a given band pass, is a function of the temperature of the incident blackbody radiation source.

The instrument function of the sensor includes the wave bands and the number of transmission surfaces for the sensor. Reflective surfaces are counted twice. The third module 254 uses the absorbance spectrum and the estimated thickness of the molecular film to convolve a Beer's law absorption with a warm source modeled by a blackbody function.

$$T_\lambda = \frac{I(\lambda)}{I_0(\lambda)} = e^{-\alpha(\lambda) \cdot t \cdot n} \quad \text{Equation 14}$$

For a given wavelength, the transmission loss can be calculated using Equation 14, where $\alpha(\lambda)$ is the absorption coefficient at the wavelength $\lambda$ (cm$^{-1}$), t is the thickness of the film and n is the total number of surfaces. The total transmission calculated by the third module over a wave band $\lambda 1$ to $\lambda 2$ is determined by Equation 15, where $L(\lambda,T)$ is the photon radiance for a given wavelength $\lambda$ and temperature T, and is defined by Equation 16. Using the results of Equation 15, the transmittance $I/I_0$ (see Equation 9) is plotted as a function of blackbody temperature, thus providing an indication of sensor degradation due to the contaminant film.

$$\tau(T) = \frac{\int_{\lambda 1}^{\lambda 2} \tau_\lambda \cdot L(\lambda, T) d\lambda}{\int_{\lambda 1}^{\lambda 2} (\lambda, T) d\lambda} \quad \text{Equation 15}$$

$$L(\lambda, T) = \frac{2\pi c}{\lambda^4 (\exp(hc/\lambda kT) - 1)} \quad \text{Equation 16}$$

Figure 17:
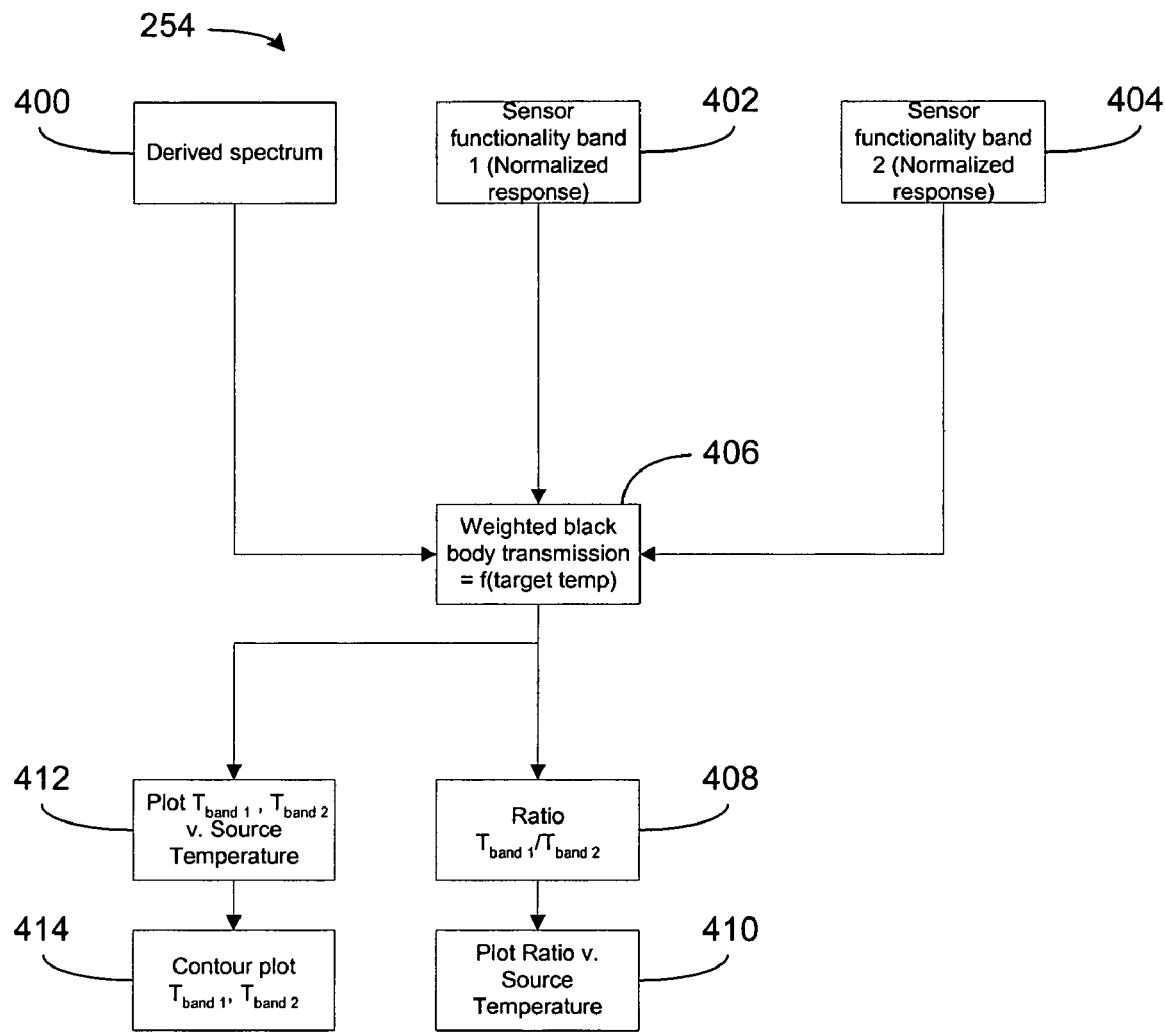
FIG. 17 is a schematic block diagram illustrating exemplary functions performed in the third module of FIG. 11.

Referring to FIG. 17, a schematic block diagram of the third module 254 is illustrated. As noted above, in order to make a determination of the transmission loss, knowledge of the IR spectral signature of the contaminant and the sensor's instrument function is required. FIG. 17 schematically demonstrates the convolution of this data showing the transmission loss for two wave bands and the change in transmission of the band pass ratio.

Beginning at block 400, the derived spectrum of the contaminant film estimated by the second module 252 is input into the third module 254. At blocks 402 and 404, the sensor functionality band 1 and band 2 are normalized as is conventional and input into the third module. At block 406, the blackbody response of each band channel is weighted by the absorption of the outgassing contaminant spectrum as a function of wavelength (block 406 represents Equation 15 above). At block 408 the ratio of the two transmission bands is calculated and at block 410 the transmission band ratio is plotted against the source temperature. At block 412, the individual transmission bands (e.g., $T_{band\ 1}$ and $T_{band\ 2}$) are plotted against the source temperature, and at block 414 a contour plot (e.g., thickness plotted against the source temperature) is constructed. The contour plot enables a designer to estimate the effects of a change in film thickness in the transmittance of the system.

Figure 18A:
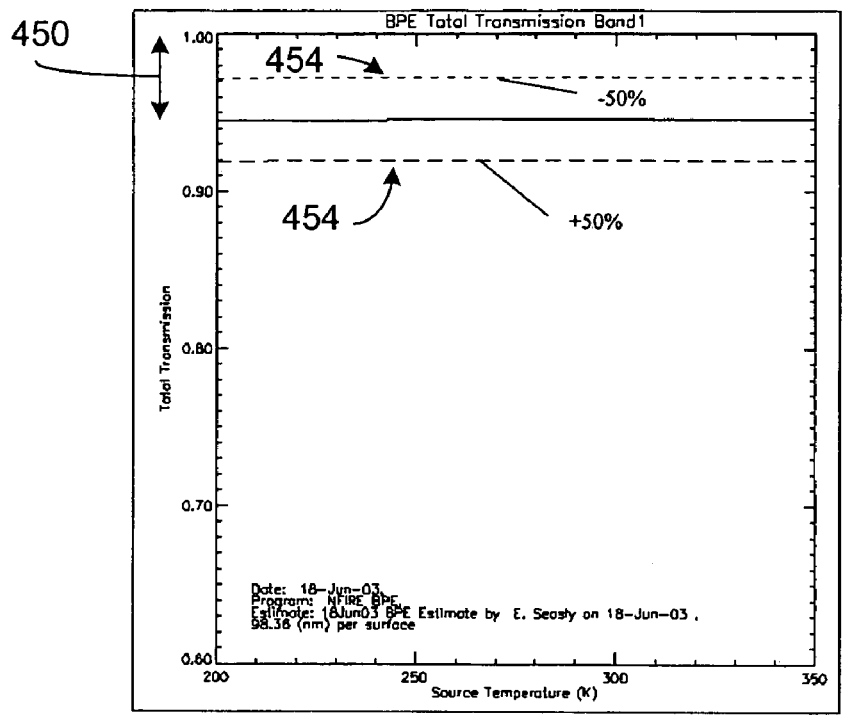
FIG. 18A is a transmission plot as a function of black body temperature for a first band of a hypothetical sensor.
Figure 18B:
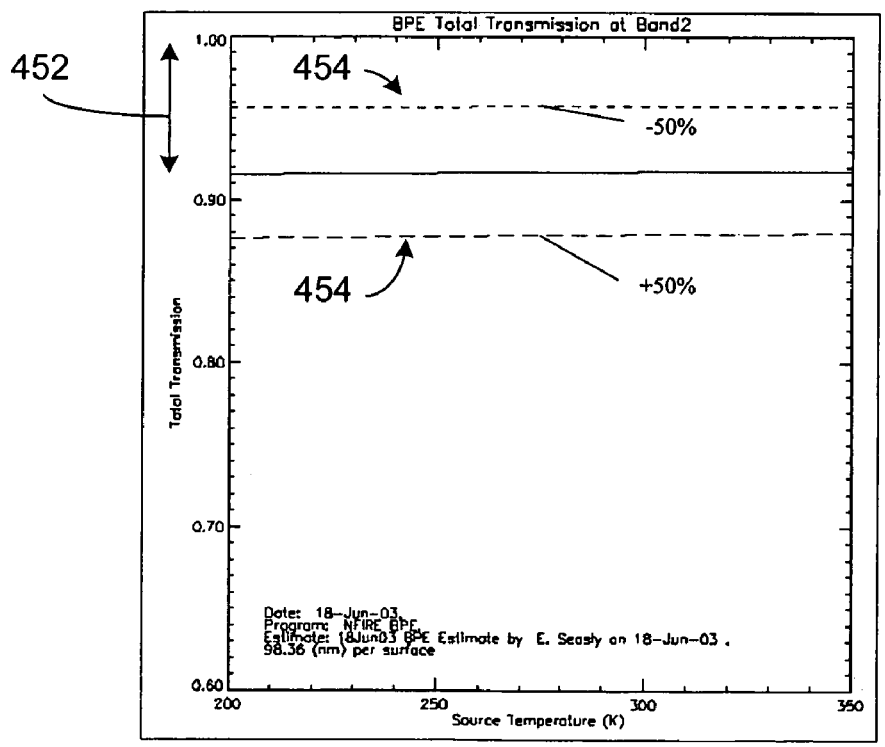
FIG. 18B is a transmission plot as a function of black body temperature for a second band of a hypothetical sensor.
Figure 18C:
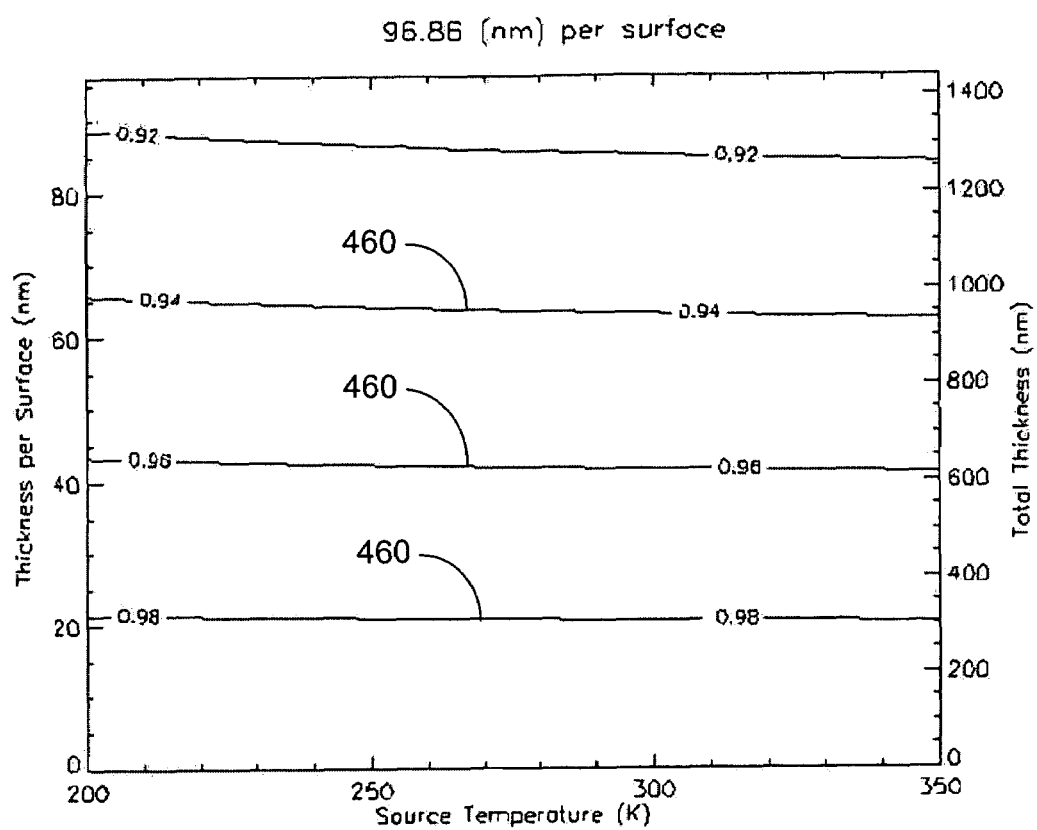
FIG. 18C is a contour plot of film thickness as a function of black body temperature.

Results of the transmission loss for two hypothetical bands (bands 1 and 2) are shown in FIGS. 18A-18C. In FIGS. 18A and 18B, the total transmission loss is plotted as a function of blackbody temperature. FIG. 18A illustrates a band 1 transmission loss 450 of 6.5%, and FIG. 18B illustrates a band 2 transmission loss 452 of 8.5%. The estimation of error is shown in the dashed lines 454 representing a 50% uncertainty in the absorption spectra. FIG. 18C illustrates the contour plot for film thickness plotted against source temperature. Each line 460 of the contour plot represents a transmission function of thickness and source temperature.

Figure 19:
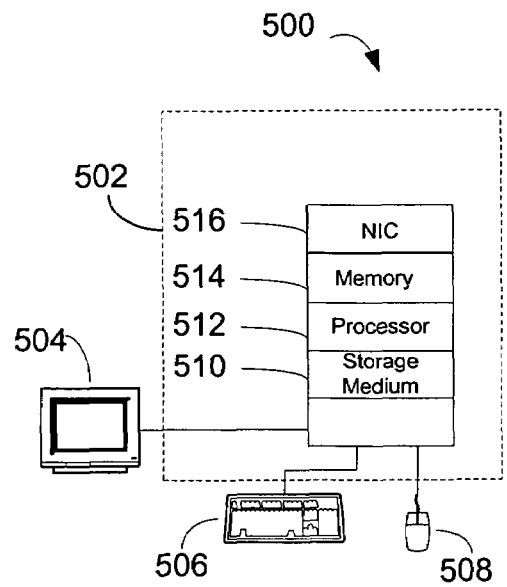
FIG. 19 illustrates an exemplary computer system used to implement the present invention.

Moving to FIG. 19 a computer system 500 for implementing the present invention is illustrated. The computer system 500 includes a computer 502 for processing data, and a display 504 for viewing system information. The technology used in the display is not critical and may be any type currently available, such as a flat panel liquid crystal display (LCD) or a cathode ray tube (CRT) display, or any display subsequently developed. A keyboard 506 and pointing device 508 may be used for data entry, data display, screen navigation, etc. The keyboard 506 and pointing device 508 may be separate from the computer 502 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 506 and pointing device 508. A touch screen is well known by those skilled in the art and will not be described in detail herein. Briefly, a touch screen implements a thin transparent membrane over the viewing area of the display 504. Touching the viewing area sends a signal to the computer 502 indicative of the location touched on the screen. The computer 502 may equate the signal in a manner equivalent to a pointing device and act accordingly. For example, an object on the display 504 may be designated in software as having a particular function (e.g., view a different screen). Touching the object may have the same effect as directing the pointing device 508 over the object and selecting the object with the pointing device, e.g., by clicking a mouse. Touch screens may be beneficial when the available space for a keyboard 506 and/or a pointing device 508 is limited.

Included in the computer 502 is a storage medium 510 for storing information, such as application data, screen information, programs, etc. The storage medium 510 may be a hard drive, for example. A processor 512, such as an AMD Athlon XP™ processor or an Intel Pentium IV® processor, combined with a memory 514 and the storage medium 510 execute programs to perform various functions, such as data entry, numerical calculations, screen display, system setup, etc. A network interface card (NIC) 516 allows the computer 502 to communicate with devices external to the system 500.

The actual code for performing the functions described herein can be easily programmed by a person having ordinary skill in the art of computer programming in any of a number of conventional programming languages based on the disclosure herein. Consequently, further detail as to the particular code itself has been omitted for sake of brevity.

While particular embodiments of the invention have been described in detail, it is understood that the invention is not limited correspondingly in scope, but includes all changes, modifications and equivalents coming within the spirit and terms of the claims appended hereto. For example, the present invention can be used to estimate the degradation in performance of a sensor due to outgassing soils on piece parts and soils introduced during manufacture and assembly. Using this information along with the performance criteria of the sensor, a cleanliness budget for manufacturing the sensor can be calculated. All or a portion of the cleanliness budget can be allocated to contaminants introduced due to pieces parts contamination and due to assembly of the sensor, for example.

What is claimed is:

1. A method of modeling the effect of a molecular contaminant film on performance of an optical system, comprising the steps of:
    correlating a mass of material outgassed from materials of the optical system to a spectrum of outgassed products;
    using the spectrum of outgassed products to predict an aggregate molecular contaminant film thickness from the outgassed material;
    deriving an absorbance spectrum of the aggregate molecular contaminant film; and
    convolving the absorbance spectrum of the aggregate molecular contaminant film with an instrument function of the optical system to obtain an estimated degradation in performance of the optical system.

2. The method of claim 1, wherein the step of predicting the aggregate molecular film thickness includes the step of summing a weighted spectrum of each individual component's outgassed product to form the aggregate molecular contaminant film.

3. The method of claim 1, wherein the step of correlating the mass of material outgassed from materials of the optical system to a spectrum of outgassed products includes the steps of:
    classifying each outgassed material into one of several groups based on at least one observed characteristic of the outgassed material; and
    obtaining an absorbance spectrum of a sample of the outgassed material; and
    estimating a thickness of the sample of outgassed material based on the absorbance spectrum and the classification of the outgassed material.

4. The method of claim 3, wherein the step of obtaining the absorbance spectrum of the sample of the outgassed material includes the step of obtaining an average absorbance spectrum of a sample of the outgassed material.

5. The method of claim 3, wherein the step of classifying each outgassed material into one of several groups includes the groups consisting of a contaminant that is a pure substance that is a liquid at room temperature (Type 1 sample), a contaminant that is not a liquid or a pure substance but spectrum indicates that an absorbance in a region of interest is dominated by a single functional group (Type 2 sample), and a contaminant whose outgassing products are not a pure substance and cannot be represented by a single model compound that is a liquid (Type 3 sample).

6. The method of claim 5, further comprising the steps of:
    estimating the thickness of the Type 1 sample based on the geometry of the Type 1 sample;
    estimating the thickness of the Type 2 sample based on a known material that has a similar absorbance spectrum as the absorbance spectrum of the Type 2 sample; and
    estimating the thickness of the Type 3 sample based on a synthetic spectrum constructed from model vectors of known materials that approximates the absorbance spectrum of the Type 3 sample.

7. The method of claim 6, wherein the step of estimating the thickness of the Type 1 sample includes the steps of estimating the thickness of the Type 1 sample based on a mass of the Type 1 sample, an area occupied by the Type 1 sample, and a density of the Type 1 sample.

8. The method of claim 6, wherein the step of estimating the thickness of the Type 2 sample includes the steps of:
    selecting a material that has a similar absorbance spectrum as the absorbance spectrum of the Type 2 sample;
    obtaining an absorbance spectrum of the selected material, wherein the thickness of the selected material is about 1 micron;
    scaling the absorbance spectrum of the sample of the selected material by a scale factor to obtain a vector that approximates the strength of the absorbance spectrum of the Type 2 sample; and
    estimating the thickness of the Type 2 sample as the product of the scale factor and the thickness of the selected material.

9. The method of claim 6, wherein the step of estimating the thickness of the Type 3 sample includes the steps of:
- combining normalized vectors for known model compounds;
- assigning a thickness to each vector;
- manipulating the thickness assigned to each vector to construct an initial synthetic spectrum that approximates the absorbance spectrum of the Type 3 sample; and
- estimating the thickness of the Type 3 sample as the summation of the thickness assigned to each vector of the initial synthetic spectrum.

10. The method of claim 9, further comprising the steps of:
- identifying an error region of the initial synthetic spectrum;
- adding at least one normalized vector for known model compounds to the initial synthetic spectrum, wherein the at least one added vector compensates for a residue in the error region of the initial spectrum;
- assigning a thickness to the at least one added vector;
- manipulating the thickness of the at least one added vector to minimize the residue in the error region of the synthetic spectrum;
- adding the manipulated thickness of the at least one vector to the estimated thickness of the Type 3 sample when the residue is positive; and
- subtracting the manipulated thickness of the at least one vector to the estimated thickness of the Type 3 sample when the residue is negative.

11. The method of claim 9, further comprising the step of weighting the thickness of each model compound by the density of the compound.

12. The method of claim 3, further comprising the step of deriving a per unit absorbance spectrum of the sample of outgassed material.

13. The method of claim 1, wherein the step of correlating the mass of material outgassed from materials of the optical system to the spectrum of outgassed products includes using an infrared spectrum of outgassed products.

14. The method of claim 1, wherein the step of correlating the mass of material outgassed from materials of the optical system to the spectrum of outgassed products includes using a mass of material outgassed from organic materials.

15. The method of claim 1, wherein correlating includes using a normalized spectrum of outgassed products.

16. The method of claim 1, further comprising plotting at least one transmission band as a function of source temperature.

17. A computer system for modeling the effect of a molecular contaminant film on performance of an optical system, comprising:
- a storage medium;
- at least one processor, wherein the processor is operatively coupled to the storage medium;
- a computer program residing on the storage medium and executed by the at least one processor, wherein the computer program causes the processor to
  - correlate a mass of material outgassed from materials of the optical system to spectrum of outgassed products;
  - use the spectrum of outgassed products to predict an aggregate molecular contaminant film thickness from the outgassed material; and
  - convolve an absorbance spectrum of the aggregate molecular contaminant film with an optical system instrument function to obtain an estimated degradation in performance of the optical system; and
  - output the estimated degradation in performance of the optical system.

18. The system of claim 17, wherein a weighted spectrum of each individual component's outgassed product is summed to predict the aggregate molecular contaminant film thickness.

19. The system of claim 17, wherein the computer program further causes the processor to:
- classify each outgassed material into one of several groups based on at least one observed characteristic of the outgassed material;
- obtain an absorbance spectrum of a sample of the outgassed material; and
- estimate a thickness of the sample of outgassed material based on the absorbance spectrum and the classification of the outgassed material.

20. The system of claim 19, wherein the computer program further causes the processor to obtain an average absorbance spectrum of a sample of the outgassed material.

21. The system of claim 19, wherein the computer program further causes the processor to classify each outgassed material into the groups consisting of a contaminant that is a pure substance that is a liquid at room temperature (Type 1 sample), a contaminant that is not a liquid or a pure substance but spectrum indicates that an absorbance in a region of interest is dominated by a single functional group (Type 2 sample), and a contaminant whose outgassing products are not a pure substance and cannot be represented by a single model compound that is a liquid (Type 3 sample).

22. The system of claim 21, wherein the computer program further causes the processor to:
- estimate the thickness of the Type 1 sample based on the geometry of the Type 1 sample;
- estimate the thickness of the Type 2 sample based on a known material that has a similar absorbance spectrum as the absorbance spectrum of the Type 2 sample; and
- estimate the thickness of the Type 3 sample based on a synthetic spectrum constructed from model vectors of known materials that approximates the absorbance spectrum of the Type 3 sample.

23. The system of claim 22, wherein the computer program further causes the processor to estimate the thickness of the Type 1 sample based on a mass of the Type 1 sample, an area occupied by the Type 1 sample, and a density of the Type 1 sample.

24. The system of claim 22, wherein the computer program further causes the processor to:
- select a material that has a similar absorbance spectrum as the absorbance spectrum of the Type 2 sample;
- obtain an absorbance spectrum of the selected material, wherein the thickness of the selected material is about 1 micron;
- scale the absorbance spectrum of the sample of the selected material by a scale factor to obtain a vector that approximates the strength of the absorbance spectrum of the Type 2 sample; and
- estimate the thickness of the Type 2 sample as the product of the scale factor and the thickness of the selected material.

25. The system of claim 22, wherein the computer program further causes the processor to:
- combine normalized vectors for known model compounds;
- assign a thickness to each vector;

manipulate the thickness assigned to each vector to construct an initial synthetic spectrum that approximates the absorbance spectrum of the Type 3 sample; and estimate the thickness of the Type 3 sample as the summation of the thickness assigned to each vector of the initial synthetic spectrum.

26. The system of claim 25, wherein the computer program further causes the processor to:

identify an error region of the initial synthetic spectrum;

add at least one normalized vector for known model compounds to the initial synthetic spectrum, wherein the at least one added vector compensates for a residue in the error region of the initial spectrum;

assign a thickness to the at least one added vector;

manipulate the thickness of the at least one added vector to minimize the residue in the error region of the synthetic spectrum;

add the manipulated thickness of the at least one vector to the estimated thickness of the Type 3 sample when the residue is positive; and subtract the manipulated thickness of the at least one vector to the estimated thickness of the Type 3 sample when the residue is negative.

27. The system of claim 24 wherein the computer program further causes the processor to weight the thickness of each model compound by the density of the compound.

28. The method of claim 19, wherein the computer program further causes the processor to derive a per unit absorbance spectrum of the sample of outgassed material.

29. The method of claim 17, wherein the computer program further causes the processor to generate a contour plot, wherein the contour plot includes the at least one transmission band plotted as a function of a source temperature for a range of aggregate molecular contaminant film thicknesses.

30. The method of claim 17, wherein the computer program further causes the processor to:

calculate a ratio of a first transmission band and a second transmission band; and plot the ratio as a function of a source temperature.

31. The system of claim 17, wherein the computer program further causes the processor to normalize the spectrum of outgassed products.

32. The system of claim 17, wherein outputting the estimated degradation in performance of the optical system includes plotting at least one transmission band as a function of source temperature.

33. A method of modeling the effect of a molecular contaminant film on performance of an optical system, comprising the steps of:

estimating an absorbance spectrum for at least one compound used to construct the optical system; and using the estimated absorbance spectrum to estimate an aggregate contaminant film thickness produced from at least one soil, wherein the at least one soil is outgassed from the at least one compound; and estimating a degradation in performance of the optical system due to the aggregate contaminant film.

34. The method of claim 33, wherein estimating the absorbance spectrum includes estimating an absorbance spectrum per unit thickness of the at least one compound.

35. The method of claim 34, further comprising using the estimated absorbance spectrum per unit thickness of the at least one compound to estimate at least one of an aggregate film thickness or an absorbance spectrum of the aggregate film thickness.

* * * * *

UNITED STATES PATENT AND TRADEMARK OFFICE
CERTIFICATE OF CORRECTION

| | | |
|---|---|---|
| PATENT NO. | : 7,319,942 B2 | Page 1 of 1 |
| APPLICATION NO. | : 10/723337 | |
| DATED | : January 15, 2008 | |
| INVENTOR(S) | : David B. Hatfield, Michael K. Burkland and Elaine E. Seasly | |

It is certified that error appears in the above-identified patent and that said Letters Patent is hereby corrected as shown below:

Col. 1 before the section "Field of Invention", please insert the following government clause:

Government Interests

Column 1, line 4, --This invention was made with the United States Government support under Contract number HQ0006-98-C-003 awarded by the Secretary of Defense. The United States Government has certain rights in this invention.--

Signed and Sealed this

Sixteenth Day of September, 2008

JON W. DUDAS
*Director of the United States Patent and Trademark Office*